US009717513B2

(12) United States Patent
Golan

(10) Patent No.: US 9,717,513 B2
(45) Date of Patent: Aug. 1, 2017

(54) FRACTURING CALCIFICATIONS IN HEART VALVES

(75) Inventor: Erez Golan, Rehovot (IL)

(73) Assignee: Pi-Cardia Ltd., Rehovot (IL)

( * ) Notice: Subject to any disclaimer, the term of this patent is extended or adjusted under 35 U.S.C. 154(b) by 1122 days.

(21) Appl. No.: 13/055,507

(22) PCT Filed: Jul. 27, 2009

(86) PCT No.: PCT/US2009/051784
§ 371 (c)(1),
(2), (4) Date: Jan. 24, 2011

(87) PCT Pub. No.: WO2010/014515
PCT Pub. Date: Feb. 4, 2010

(65) Prior Publication Data
US 2011/0118634 A1 May 19, 2011

Related U.S. Application Data

(60) Provisional application No. 61/083,934, filed on Jul. 27, 2008, provisional application No. 61/096,061, (Continued)

(51) Int. Cl.
*A61B 17/22* (2006.01)
*A61B 17/3207* (2006.01)
(Continued)

(52) U.S. Cl.
CPC ............ *A61B 17/22012* (2013.01); *A61B 17/320725* (2013.01); *A61F 2/2427* (2013.01);
(Continued)

(58) Field of Classification Search
USPC .......... 623/1.11, 1.24, 1.26, 2.37, 2.36, 2.38, 623/1.3; 606/108, 194, 200, 169, 167,
(Continued)

(56) References Cited

U.S. PATENT DOCUMENTS

| 4,484,579 A | 11/1984 | Meno et al. |
| 5,295,958 A * | 3/1994 | Shturman ........ A61B 17/22012 604/103.07 |

(Continued)

FOREIGN PATENT DOCUMENTS

| WO | WO99/44512 | 9/1999 |
| WO | WO2007/149905 | 12/2007 |

*Primary Examiner* — Jocelin Tanner
(74) *Attorney, Agent, or Firm* — Dekel Patent Ltd.; David Klein

(57) ABSTRACT

A device for fracturing calcifications in heart valves including a catheter (12, 22, 42) configured for percutaneous delivery to a heart valve, an fracture-producing element (14, 26, 46, 64, 66, 82, 124, 152) disposed at a distal portion of the catheter and operative to vibrate and mechanically fracture calcifications when brought into contact with a calcification at a leaflet of the heart valve, and an energy source (34, 47, 79, 98, 152) operative to vibrate the fracture-producing element so that the fracture-producing element fractures the calcification without necessarily removing the calcification from the leaflet. The device may further comprise a valvuloplasty balloon (30), an embolic protection net (56) and a protective sleeve (110, 130).

19 Claims, 25 Drawing Sheets

Related U.S. Application Data filed on Sep. 11, 2008, provisional application No. 61/162,343, filed on Mar. 23, 2009.

(51) Int. Cl.
 *A61B 17/00* (2006.01)
 *A61F 2/24* (2006.01)

(52) U.S. Cl.
 CPC ........... *A61B 2017/00243* (2013.01); *A61B 2017/00535* (2013.01); *A61B 2017/00783* (2013.01); *A61B 2017/22051* (2013.01); *A61B 2017/22069* (2013.01); *A61B 2017/22097* (2013.01); *A61B 2017/22098* (2013.01); *A61B 2017/320716* (2013.01); *A61F 2/2418* (2013.01)

(58) Field of Classification Search
 USPC ...... 606/27, 45, 191, 198, 127, 128, 41, 159; 601/4; 604/93.01, 508, 506, 507, 27, 604/509, 22; 310/50; 600/469, 462, 471; 318/400.38, 400.39; 607/122
 See application file for complete search history.

(56) References Cited

U.S. PATENT DOCUMENTS

| | | | | |
|---|---|---|---|---|
| 5,649,941 A * | 7/1997 | Lary | ................. | A61B 17/3207 604/22 |
| 5,728,123 A * | 3/1998 | Lemelson | ........ | A61B 17/32072 604/101.01 |
| 5,827,269 A * | 10/1998 | Saadat | ................... | A61B 18/00 606/28 |
| 5,846,218 A * | 12/1998 | Brisken | ............ | A61B 17/22012 604/22 |
| 5,916,229 A * | 6/1999 | Evans | ................ | A61B 10/0275 600/564 |
| 6,022,336 A * | 2/2000 | Zadno-Azizi | .......... | A61B 17/22 604/101.05 |
| 2002/0125842 A1* | 9/2002 | Hong | .................... | H02K 7/063 318/114 |
| 2003/0229370 A1 | 12/2003 | Miller et al. | | |
| 2004/0230117 A1 | 11/2004 | Tosaya et al. | | |
| 2005/0021015 A1 | 1/2005 | Keidar et al. | | |
| 2005/0075662 A1* | 4/2005 | Pedersen | ................ | A61B 17/22 606/194 |
| 2005/0085847 A1* | 4/2005 | Galdonik | .................. | A61F 2/01 606/200 |
| 2005/0137696 A1* | 6/2005 | Salahieh | ................. | A61F 2/013 623/2.11 |
| 2005/0228418 A1* | 10/2005 | Noriega | ......... | A61B 17/320758 606/159 |
| 2005/0267488 A1 | 12/2005 | Hare et al. | | |
| 2006/0058872 A1* | 3/2006 | Salahieh | ............... | A61F 2/2418 623/2.18 |
| 2006/0229659 A1* | 10/2006 | Gifford | ................. | A61B 18/02 606/200 |
| 2006/0253148 A1* | 11/2006 | Leone | ............. | A61B 17/12022 606/200 |
| 2010/0198211 A1* | 8/2010 | Kassab | ......... | A61B 17/320725 606/32 |

* cited by examiner

26

Calcification near the leaflet edge

Calcification at the leaflet base

Leaflet

26

Leaflet

Calcified fragments

Fused commissure
82
Leaflet
Calcified lesion

Fused commissure
82
Fractured calcific deposit

98 GENERATOR
97
96
99
90
94
92

FRACTURING CALCIFICATIONS IN HEART VALVES

CROSS-REFERENCE TO RELATED APPLICATIONS

This application claims priority under 35 USC §119 to U.S. Provisional Patent Application, Ser. No. 61/083,934, filed 27 Jul. 2008, U.S. Provisional Patent Application, Ser. No. 61/096,061, filed 11 Sep. 2008, U.S. Provisional Patent Application, Ser. No. 61/162,343, filed 23 Mar. 2009, and is a national phase application of PCT/US2009/051784, filed 27 Jul. 2009.

FIELD OF THE INVENTION

The present invention generally relates to percutaneous devices and methods for fracturing calcifications in heart valves, such as aortic valve leaflets.

BACKGROUND OF THE INVENTION

Reference is made to FIG. 1, which illustrates the anatomy of a calcified aortic valve, ascending aorta and aortic arch. Calcifications may be embedded and/or superimposed on the valve leaflets, which are connected to the aortic wall just below the coronary ostia.

Reference is now made to FIG. 2, which illustrates an enlarged view of a calcified aortic valve. The leaflets create concave sinuses on their aortic aspect, just below the coronary ostia. Calcification can be either embedded or superimposed on the leaflets, making the leaflets thicker and less pliable. Specifically, calcification that occurs at the leaflet base, i.e., where the leaflet connects to the annulus or aortic wall, can significantly impair the mobility of the leaflet, very much like friction in a door-hinge.

Reference is now made to FIG. 3, which illustrates the anticipated effect of using a balloon valvuloplasty device (prior art) in order to dilate the valve. The balloon is not designed to fracture the calcification, and therefore produces only a limited "stretching" effect on the leaflets and annulus. Such a "stretching" effect may have limited effectiveness and durability, can potentially cause tearing of the fibrous tissue that makes up most of the leaflets, and might even press the calcification against the AV node, leading to pacing complications.

Reference is now made to FIG. 4, which illustrates a typical outcome in the prior art when implanting a trans-catheter stent-mounted valve inside a heavily calcified native valve (either with or without conventional balloon valvuloplasty as a preceding step). The heavy calcification on the native valve leaflets remains intact, preventing the implanted stent-mounted valve from fully expanding. When the implanted valve stent does not expand properly, the implanted valve cross-sectional area will be smaller, the coaptation of the implanted valve leaflets will be sub-optimal, and significant paravalvular leaks may occur due to the remaining gaps between the implanted valve stent and the native valve leaflets. Each and all of these factors might significantly sacrifice the short-term and long-term outcome of the trans-catheter valve implantation procedure.

SUMMARY OF THE INVENTION

The present invention seeks to provide improved percutaneous devices and methods that may be used for fracturing calcifications in aortic valve leaflets, in order to increase leaflet pliability and mobility, thereby increasing the cross-sectional area of the open valve in patients with aortic stenosis. In addition, the devices and methods described can be applied as a preparation step for trans-catheter aortic valve implantation, in order to allow valve implantation in heavily calcified native valves, increase the cross-sectional area of the implanted valve and decrease the risk of paravalvular leaks. The devices and methods may also be designed for performing angioplasty on calcified plaque.

Some embodiments of the invention consist of percutaneous devices and methods for selectively fracturing, sawing through, dilating and possibly retrieving calcified aortic valve leaflets. The invention can potentially be useful for improving the safety, effectiveness and outcome of percutaneous aortic valve replacement procedures, specifically in cases of significant asymmetric calcification or bicuspid valves. The invention may also be used as a stand alone procedure for patients with aortic stenosis.

Some embodiments of the invention consist of devices and methods that can be used to significantly improve the safety and efficacy of percutaneous implantation of aortic valves. In particular the invention describes a percutaneous protection sleeve that can be positioned in the aorta, through which large profile devices such as aortic valves, can be delivered without scraping the potentially calcified aortic wall. The sleeve can also be used to accurately position the new valve for deployment by guiding the new valve into the center of the native valve and by using markers on the sleeve that correspond to relevant anatomical features. The protection sleeve can also create an enclosed region above the native valve leaflets and below the coronary ostia, in order to capture any emboli that might be created during manipulation of the calcification in the valve, dilation or implantation of the new valve. The invention further includes devices and methods that can assist in fracturing calcified native valves in order to better dilate the valve prior to implanting the new valve, or even as a stand-alone procedure when a new valve does not need to be implanted.

There is provided in accordance with an embodiment of the invention a method for improving valve leaflet mobility by fracturing calcifications without necessarily removing the fractured calcifications. The method makes calcified leaflets more flexible by generating impact on the leaflets and fracturing the calcifications. The fractured calcifications are reduced to a size small enough that they may be safely left at the site of the leaflets without having to remove them. That is, the size is small enough so as not to cause any unsafe obstruction in blood flow or healthy functioning of the valves. Thus, the fractured calcifications may be left in the leaflet or alternatively may be removed (e.g., by drawing them away). The method may be used as a preparation step prior to new valve implantation (reducing leaks, improving durability, increasing cross sectional area, and others). The term "fracture" refers to any kind of reduction in size, such as but not limited to, fracturing, pulverizing, breaking, grinding, chopping and the like.

There is provided in accordance with an embodiment of the invention a device for fracturing calcifications in heart valves including a catheter configured for percutaneous delivery to a heart valve, a fracture-producing element disposed at a distal portion of the catheter and operative to vibrate and mechanically fracture calcifications when brought into contact with a calcification at a leaflet of the heart valve, and an energy source operative to vibrate the fracture-producing element so that the fracture-producing element fractures the calcification without necessarily removing the calcification from the leaflet.

In accordance with an embodiment of the invention, the fracture-producing element includes a high velocity impact-producing element. (Embodiments are described below for a high velocity impact-producing element, but the invention is not limited to such an element.) The fracture-producing element can mechanically fracture calcifications simultaneously at more than one region of the heart valve.

BRIEF DESCRIPTION OF THE DRAWINGS

The present invention will be understood and appreciated more fully from the following detailed description, taken in conjunction with the drawing in which:

in FIG. 30, the extendable fracturing arms are gradually extended and then activated to fracture calcification in the valve; and in FIG. 31, the protective sleeve is deployed, and the fracturing arms are retracted back into the catheter.

DETAILED DESCRIPTION OF EMBODIMENTS

Figure 5:
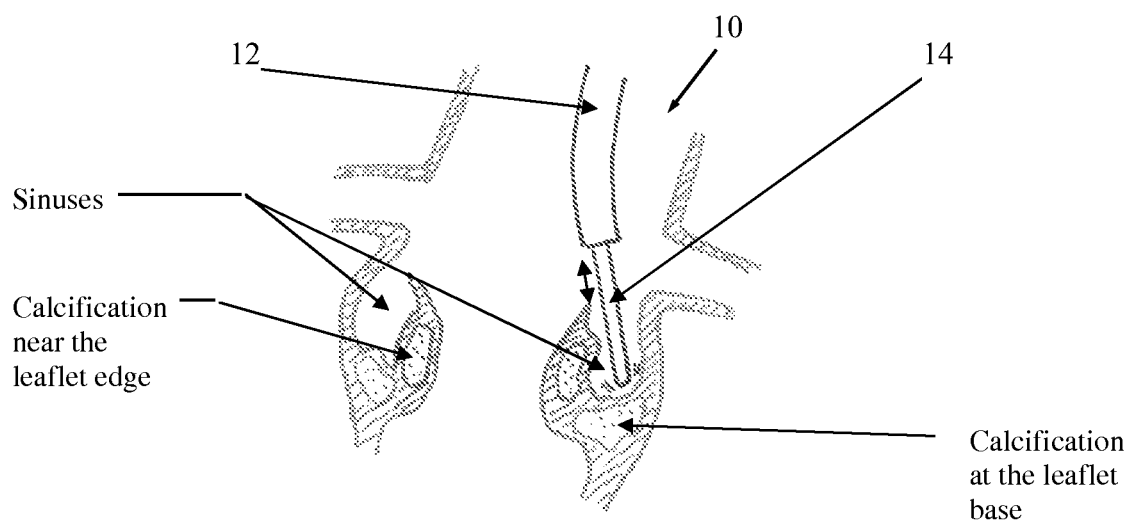
FIG. 5 is a simplified illustration of a percutaneous device for fracturing calcifications in heart valves, in accordance with a non-limiting embodiment of the present invention.

Reference is now made to FIG. 5, which illustrates a percutaneous device 10 for fracturing calcifications in heart valves, in accordance with a non-limiting embodiment of the present invention. Device 10 is a catheter-based impactor device (impactor catheter) that includes an external housing 12 (shaped as a shaft, and also referred to as shaft 12) in which is housed, and from which is deployed, an impact-producing element 14. Impact-producing element 14 creates a mechanical impact when brought into contact with hard tissue. The mechanical impact is created by a rapid back and forth vibratory motion of the impact-producing element 14. The amplitude of this vibratory motion may be small (typically from less than a millimeter and up to a few millimeters), but the velocity of the impact-producing element 14 when moving in the forward direction is relatively high. Such rapid forward motion makes the impact-producing element 14 very effective in fracturing hard tissue, such as valve calcification, while producing minimal or no effect on soft tissue, such as fibrous leaflet tissue or the aortic wall. In FIG. 5, a basic rod-shaped impact producing element 14 is delivered using the external shaft 12 into the sinus, until contact is made with the leaflet base. When the impactor is activated, the impact-producing element 14 vibrates and hits the calcification near or at the leaflet base, breaking it into smaller fragments (see FIG. 7). There are several methods to produce the vibratory motion, as will be described in what follows.

Figure 6:
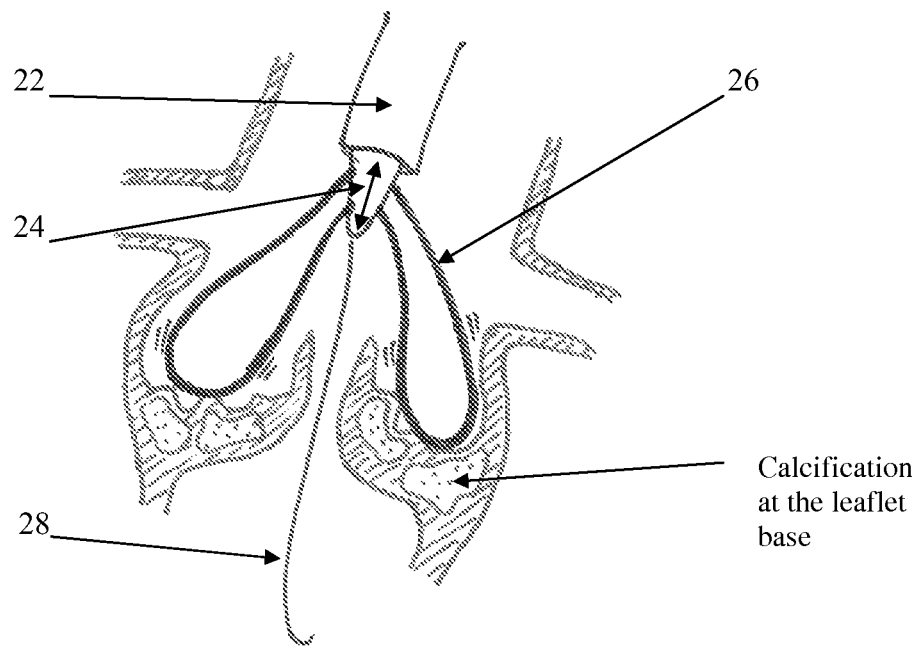
FIG. 6 is a simplified illustration of another version of the percutaneous device of FIG. 5, which may be suitable for fracturing valve calcification simultaneously within several valve leaflets.

Reference is now made to FIG. 6, which illustrates another version of the percutaneous device, which may be suitable for fracturing valve calcification simultaneously within several valve leaflets. An impact-producing element 24 (e.g., an impact-delivering shaft) is free to move/vibrate back and forth within an external housing (external shaft) 22. An energy source and mechanism at the proximal (or distal) portion of the catheter (see FIG. 12) produces this vibratory motion of the impact-delivering shaft. In order to effectively transfer the impact to several leaflets simultaneously (specifically along the leaflet bases), one or more impact-producing wire-loops (arcuate arms) 26 can be used, which extend from the distal end of impact-producing element 24. Such loops 26 are designed to be stiff enough so that when they are connected to the vibrating impact-delivering shaft 24 on their proximal side, they can transfer impact effectively to their distal tip, where they hit the calcification. At the same time, the wire loops 26 can be designed to be flexible enough so that they can be delivered into the patient in a folded (retracted) state within the external shaft 22, and then upon reaching the valve, the loops 26 can be expanded into the sinuses so they simultaneously cover all leaflet bases. The entire catheter can be delivered and retracted using a conventional guide-wire 28. Suitable materials for constructing loops 26 with the requisite blend/combination of stiffness and flexibility include, without limitation, NITINOL, stainless steel, plastic, and others. Heat treatment can be used for attaining hardness near the distal tips while retaining flexibility at other portions of the loops. Several techniques well-known in the art are available for creating a proper self-expanding shape to the loops, such as heat treatment, etc. Alternative shapes and mechanisms, such as metal meshes, spheres, rods, etc. can be used instead of simple wire loops (not shown here) in order to most effectively transfer the impact to the calcification.

Figure 7A:
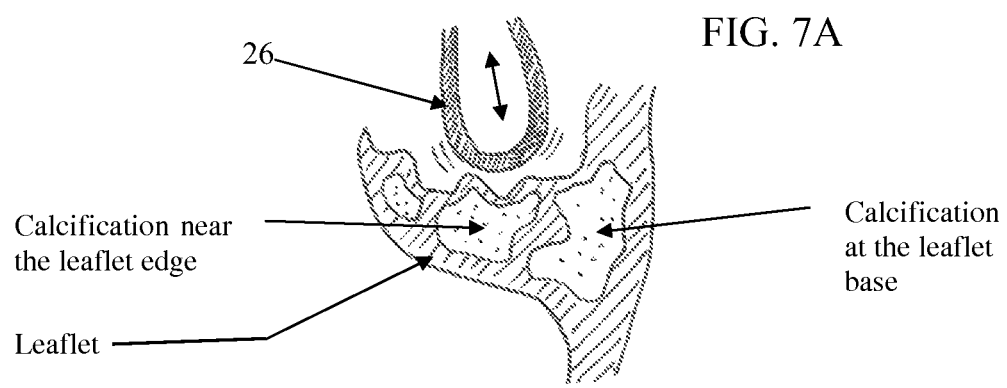
FIGS. 7A-7B are simplified illustrations of the leaflets before and after the effect produced by an impact-producing wire-loop of the device of FIG. 5.
Figure 7B:
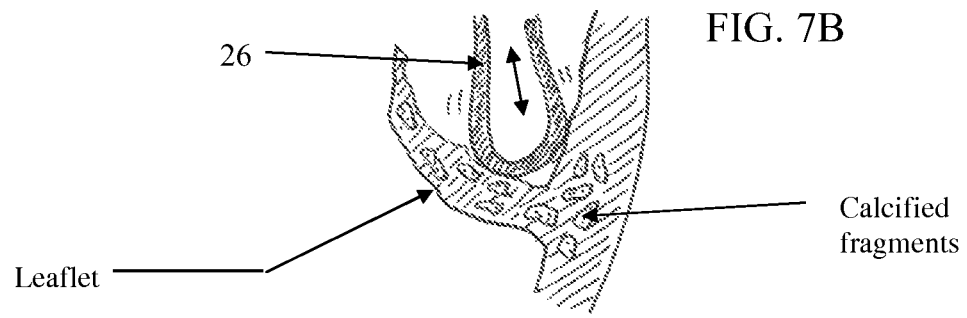

Reference is now made to FIGS. 7A-7B, which respectively illustrate the leaflets before and after the effect produced by the impact-producing wire-loop 26. Before the application of impact, large calcifications may exist within the leaflet bases or near the leaflet edges. After applying the impact, the calcifications may be fragmented into smaller deposits, making the leaflet thinner and more pliable.

Figure 8:
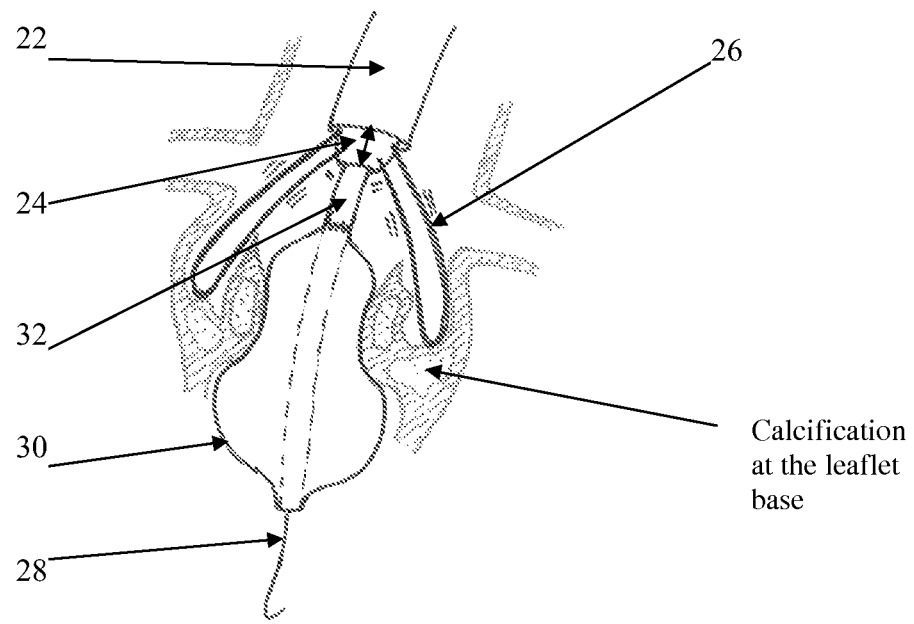
FIG. 8 is a simplified illustration of another version of the embodiment of FIG. 6.

Reference is now made to FIG. 8, which illustrates another version of the embodiment of FIG. 6. This version includes a valvuloplasty balloon 30 for simultaneous fracturing and dilation of the valve. The balloon (or any other component placed underneath the leaflets) can also be used as an anvil against which the leaflet calcification is struck by the impact-producing wire loops. The catheter includes three separate shafts that can be moved back and forth with respect to one another. The external shaft 22 is used for delivering and positioning the catheter, such as via guide-wire 28. The impact-delivering (moving) shaft 24 is used for delivering the mechanical impact from the energy source (located more proximally, see for example FIG. 12) to the impact-producing wire loops 26. The wire loops 26 can be folded out so they make contact and transfer the impact simultaneously to all leaflets. Balloon 30 is disposed on a valvuloplasty balloon shaft 32 (having a suitable lumen for passing therethrough a fluid for inflating balloon 30). Shaft 32 can be delivered through the impact-delivering shaft 24 so that when balloon 30 is inflated the leaflets are pushed aside. Once balloon 30 is inflated, the impact-producing wire loops 26 are activated to fracture the calcification within the leaflets, allowing the leaflets to gradually become thinner and more pliable, and enabling balloon 30 to gradually dilate the valve more effectively. Using balloon 30 to dilate the valve simultaneously with fracturing the calcification may be advantageous, because balloon 30 presses the leaflets against the impact-producing wire-loops 26, minimizing relative motion, increasing the fracturing effect by generating tension on the leaflets and by being used as an anvil, and also giving the operator real-time feedback on the progress of the valve dilation. The valvuloplasty balloon 30 and its delivery system can be either an integral part of the impactor device or a separate device used in conjunction with the impactor device.

Figure 9:
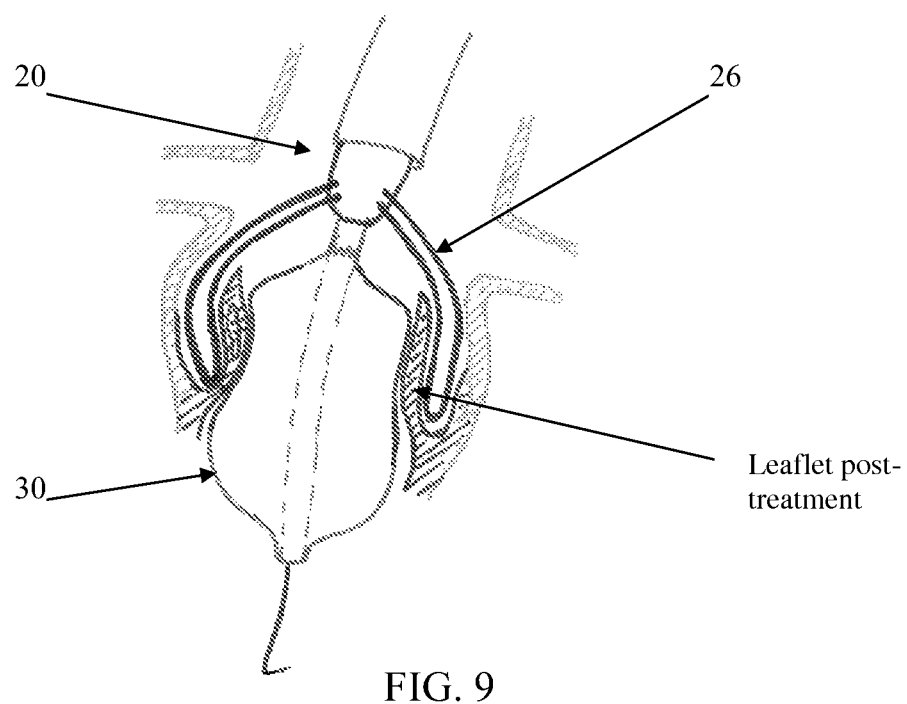
FIG. 9 is a simplified illustration of the valve after treatment with the impactor catheter of FIG. 8.

Reference is now made to FIG. 9, which illustrates the valve after treatment with the impactor catheter of FIG. 8. The leaflets are now thinner and more pliable, allowing balloon 30 to dilate the valve further.

Figure 10:
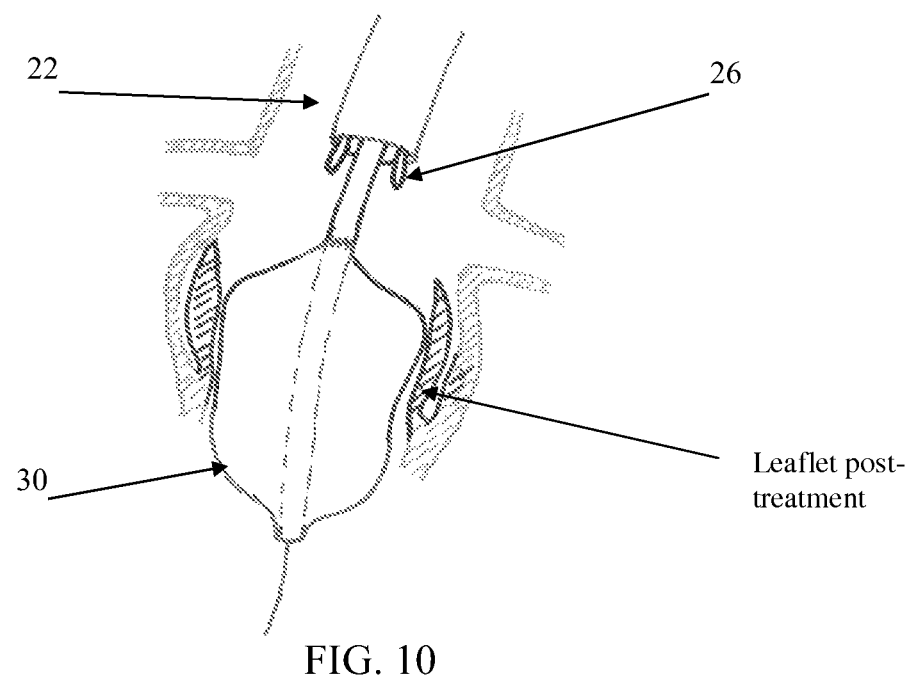
FIG. 10 is a simplified illustration of the valve after treatment with the impactor catheter of FIG. 8, after wire loops have been folded back into an external shaft.

Reference is now made to FIG. 10, which illustrates the valve after treatment with the impactor catheter of FIG. 8, after the wire loops 26 have been folded back into external shaft 22. Balloon 30 can now fully expand to dilate the valve even further. The improved outcome, in terms of increased open valve cross-sectional area, safety and durability, can be achieved as a stand-alone procedure for patients with aortic stenosis, or as a preparatory step for trans-catheter valve implantation.

Figure 1:
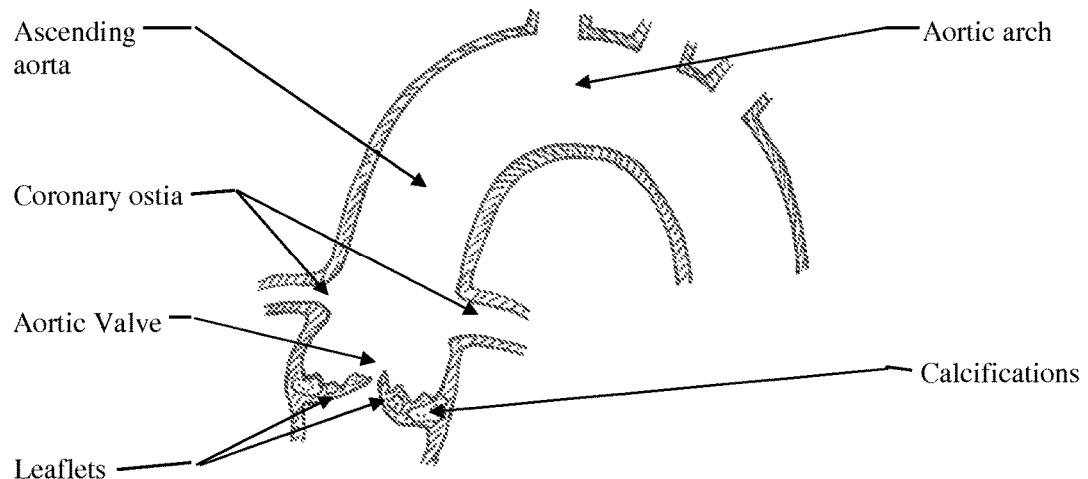
FIG. 1 is a simplified illustration of the anatomy of a calcified aortic valve, ascending aorta and aortic arch.
Figure 2:
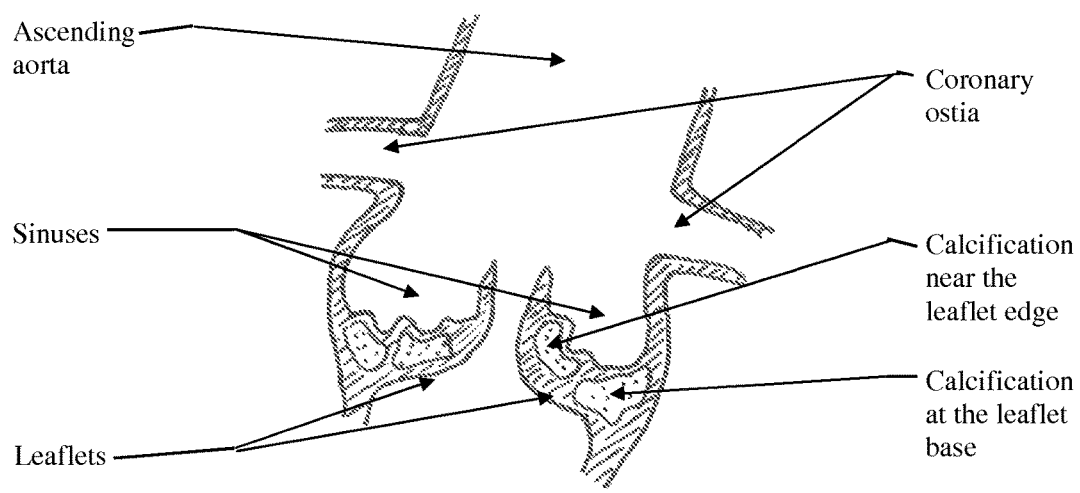
FIG. 2 is an enlarged view of a calcified aortic valve.
Figure 3:
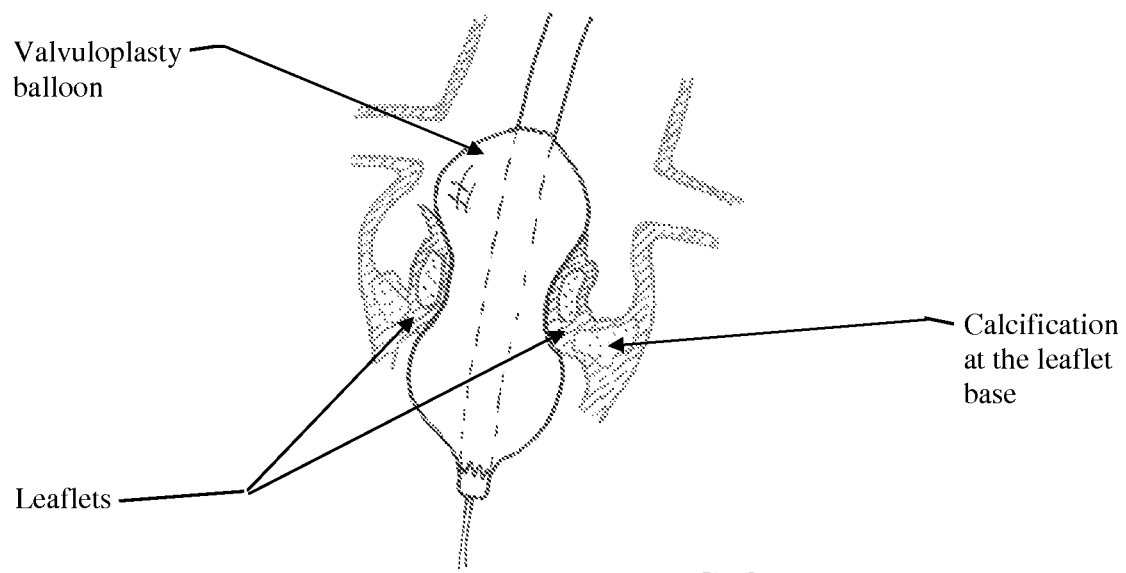
FIG. 3 is a simplified illustration of the anticipated effect of using a balloon valvuloplasty device of the prior art in order to dilate the valve.
Figure 4:
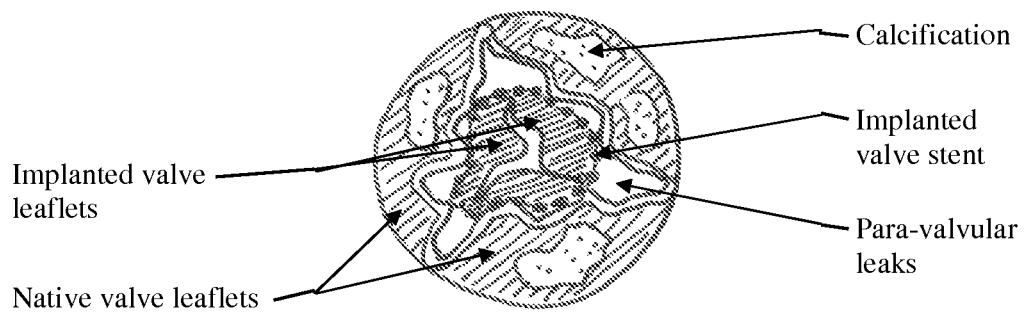
FIG. 4 is a simplified cross-sectional view of the typical outcome when implanting a trans-catheter stent-mounted valve inside a heavily calcified native valve (either with or without conventional balloon valvuloplasty as a preceding step), in the prior art.
Figure 11:
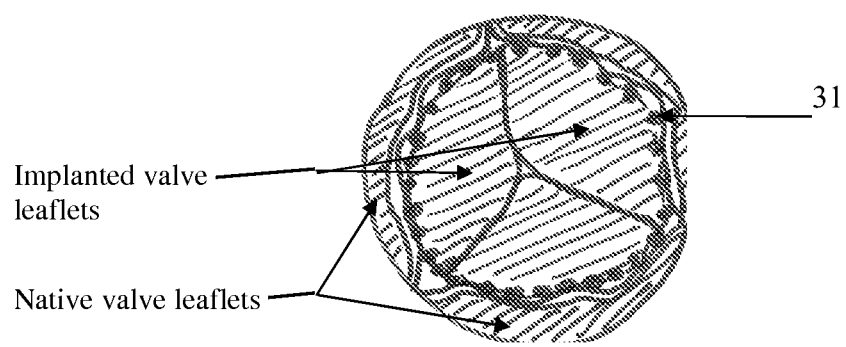
FIG. 11 is a simplified cross-sectional view of the significantly improved outcome when implanting a trans-catheter valve or valve stent inside the previously calcified valve, after having treated it with the impactor catheter of the present invention (as compared with the untreated valve shown in FIG. 4).

Reference is now made to FIG. 11, which illustrates a cross-sectional view of the significantly improved outcome when implanting a trans-catheter valve or valve stent 31 inside the previously calcified valve, after having treated it with the impactor catheter (as compared with the untreated valve shown in FIG. 4) The heavy calcification on the native valve has been fragmented, allowing the implanted valve to fully expand, increasing its cross-sectional area, improving the coaptation of the implanted valve leaflets, and significantly reducing paravalvular leaks. Each and all of these factors may significantly improve both the short-term and long-term outcome of the trans-catheter valve implantation procedure.

Figure 12:
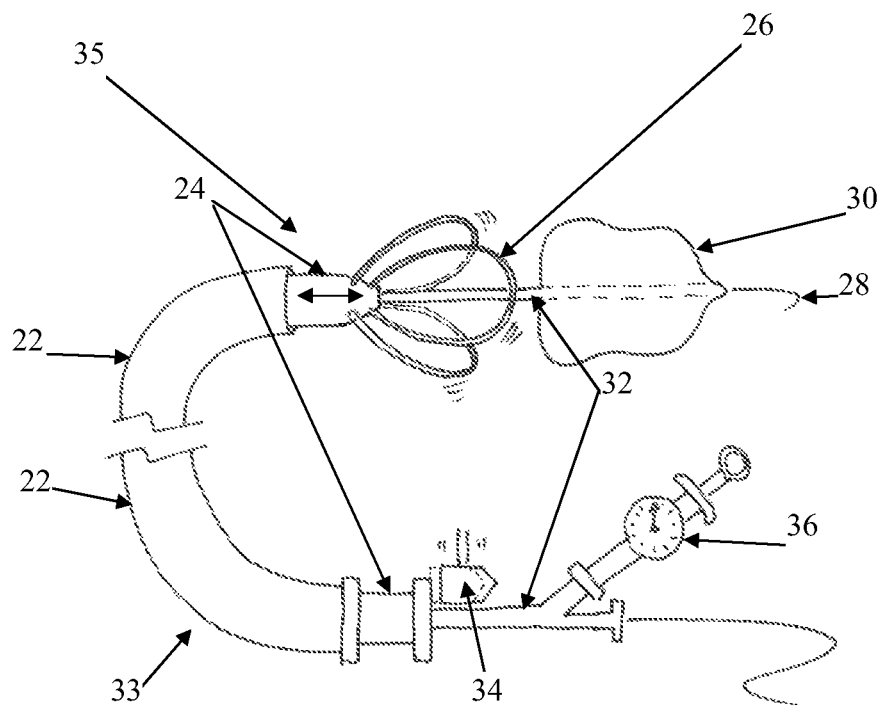
FIG. 12 is a simplified illustration of proximal and distal parts of one embodiment of the impactor catheter of FIG. 8, in accordance with an embodiment of the invention.

Reference is now made to FIG. 12, which illustrates both proximal and distal parts of one embodiment of the impactor catheter of FIG. 8. The external shaft 22 covers the entire length of the catheter. The impact-delivering shaft 24 goes through the external shaft 22 and is designed to transfer vibrations and impact created by an impact source (energy source) 34 on the proximal part 33 of the catheter, all the way to the impact-producing wire loops 26 on the distal part 35 of the catheter. The impact source 34 can be any energy source or mechanism known in the art for creating back and forth movement of the impact-delivering shaft 24, such as but not limited to, pneumatic (gas pressure and piston), hydraulic, electro-magnetic (coil and magnet), piezoelectric, electrical discharge (spark-gap), manual (with or without a spring-loaded mechanism), ultrasonic transducer, and others. The selection of mechanism and energy source depends, amongst other factors, on the required movement pattern of the impact-delivering shaft (frequency, amplitude, velocity of forward and backward movement, impact force, etc.). Alternatively, the impact source can be located at the distal part of the catheter (not shown), e.g. a miniature pneumatic piston integrated into the distal tip and activated by air that is pumped into the internal part of the catheter, or an electromagnet at the distal tip, which is driven by electrical current, etc. A pump 36 is provided for inflating balloon 30.

Figure 13:
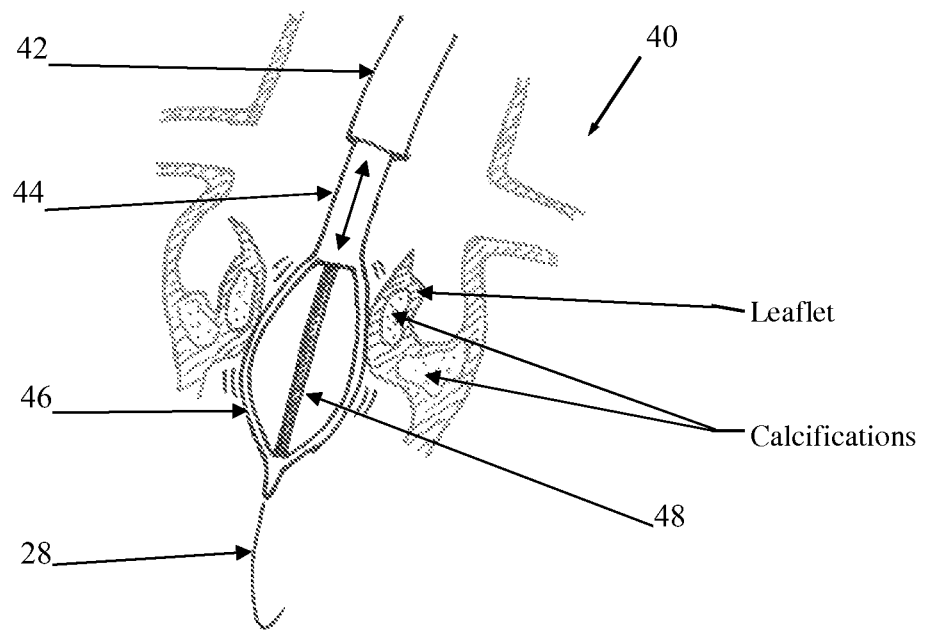
FIG. 13 is a simplified illustration of a percutaneous device (another impactor catheter) for fracturing calcifications in heart valves, in accordance with another non-limiting embodiment of the present invention.

Reference is now made to FIG. 13, which illustrates a percutaneous device 40 (another impactor catheter) for fracturing calcifications in heart valves, in accordance with another non-limiting embodiment of the present invention. Device 40 can simultaneously dilate the valve and fracture the calcifications within the leaflets. An external shaft 42 covers most of the length of the catheter and is used for delivering the catheter to the valve, potentially over a guide-wire 28. One or more impact-producing wire loops or arches (arcuate arms) 46 are connected on their proximal side to an impact-delivering (moving) shaft 44, and on their distal side to another internal shaft 48. When the internal shaft 48 is pulled backwards (distally) with respect to the impact-delivering shaft 44, the distance between the distal and proximal ends of the wire-arches 46 is shortened, and the arches 46 are forced to bend and to push the valve leaflets aside so the valve is dilated. When the wire arches 46 are bent so that sufficient contact is made between the wire arches 46 and the valve leaflets, and sufficient force is applied to push the leaflets aside, then the impact-delivering shaft 44 can be further used to deliver impact or vibrations through the wire arches 46 to the leaflets in order to fracture the calcifications. Any back and forth movement of the impact-delivering shaft 44 will be translated by the wire arches 46 into a lateral vibration or impact on the leaflets. This embodiment of the impactor catheter can therefore be used to simultaneously dilate the valve by increasing the pull on the internal shaft 48, while fracturing the calcifications by delivering impact to the wire arches 46 through the impact-delivering shaft 44. Several variations to this design can be readily made, such as using a net-like wire mesh instead of wire arches, or even a balloon within the arches. It is also possible, of course, to "reverse" the function of the shafts, i.e. to apply the impact to the internal shaft while fixing the impact-delivering shaft, etc.

Figure 14:
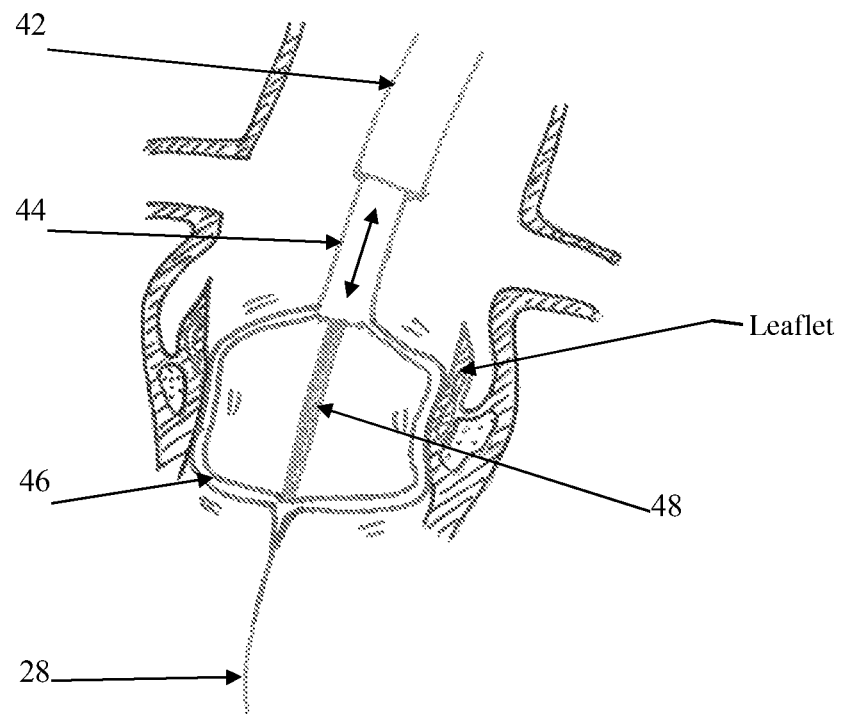
FIG. 14 is a simplified illustration of the outcome of using the impactor catheter described in FIG. 13.

Reference is now made to FIG. 14, which illustrates the outcome of using the impactor catheter described in FIG. 13. Most calcifications in the leaflets have been fractured, making the leaflets more pliable and allowing the valve to open, as the wire arches 46 are extended sideways by pulling the internal shaft 48 further into the catheter.

Figure 15:
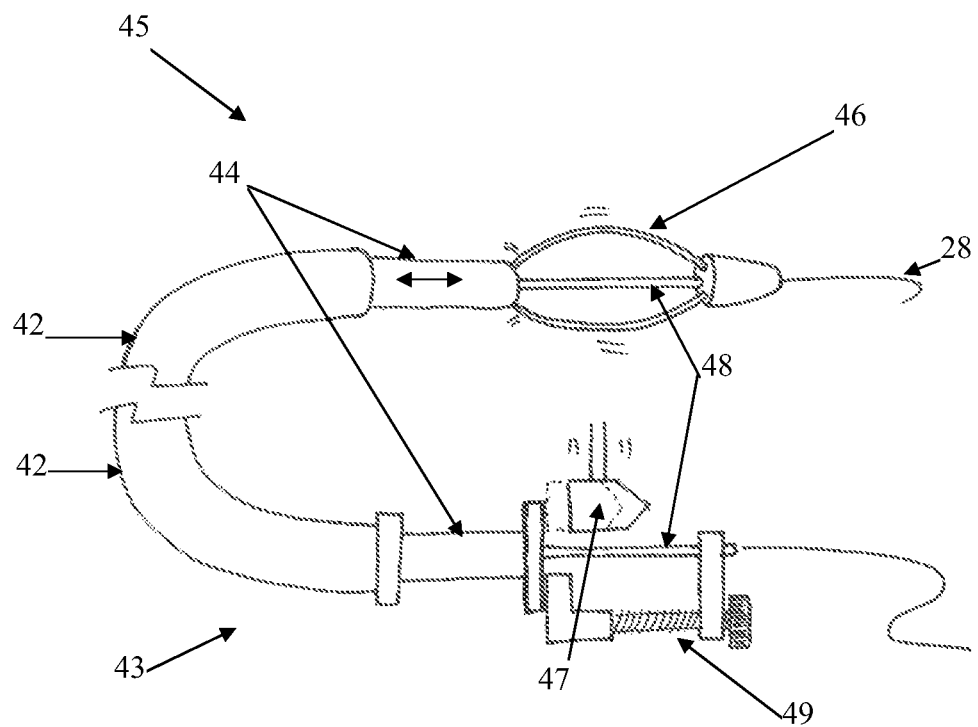
FIG. 15 is a simplified illustration of both proximal and distal parts of the impactor catheter of FIG. 13, in accordance with a non-limiting embodiment of the invention.

Reference is now made to FIG. 15, which illustrates both proximal and distal parts 43 and 45, respectively, of the impactor catheter of FIG. 13 in accordance with a non-limiting embodiment of the invention. The external shaft 42 covers most of the length of the catheter. The impact-delivering shaft 44 goes through the external shaft 42 and is designed to transfer vibrations and impact created by an impact source 47 on the proximal part 43 of the catheter, all the way to the impact-producing wire arches 46 on the distal part 45 of the catheter. The impact source 47 can be any energy source or mechanism known in the art for creating back and forth movement of the impact-delivering shaft, such as but not limited to, pneumatic (gas pressure and piston), hydraulic, electro-magnetic (coil and magnet), piezoelectric, electrical discharge (spark-gap), manual (with or without a spring-loaded mechanism), ultrasonic transducer, and others. The selection of mechanism and energy source depends, amongst other factors, on the required movement pattern of the impact-delivering shaft (frequency, amplitude, velocity of forward and backward movement, impact force, etc.). In addition, a dilation mechanism 49 is provided on the proximal side 43 of the catheter, which allows an operator-controlled, gradual extension of the wire arches 46 by pulling the internal shaft 48 with respect to the impact-delivering shaft 44, such as by using a screw-based mechanism. As the screw is turned, the internal shaft 48 is gently pulled so that the distance between the proximal and distal ends of the wire arches 46 is shortened and the arches 46 are forced to bend and extend sideways. Upon setting the arch position using the dilation mechanism 49, the impact source 47 can be activated to fracture the calcifications, and the arch position can be further increased, and so forth. Numerous other techniques can be used for extending the wire arches 46, while delivering impact to fracture the calcifications.

Figure 16:
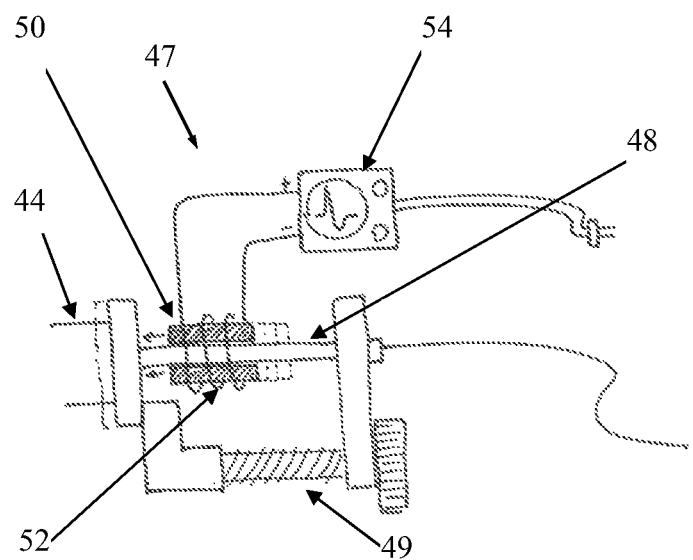
FIG. 16 is a simplified illustration of one example of an impact source for the device of FIG. 13, in accordance with a non-limiting embodiment of the invention.

Reference is now made to FIG. 16, which illustrates one example of impact source 47, namely an electromagnetic impact source. A cylindrical permanent magnet 50 can slide freely back and forth over the proximal side of internal shaft 48, so as to repeatedly strike impact-delivering shaft 44, thereby generating impact percussions that are delivered by impact-delivering shaft 44 to the distal part of the catheter. An electrical coil 52 surrounds magnet 50, so that when current is driven through the coil 52, it generates back and forth movement of magnet 50. A current source 54 is connected to coil 52, and allows control over important parameters such as impact frequency, current waveform, amplitude, etc.

Figure 17:
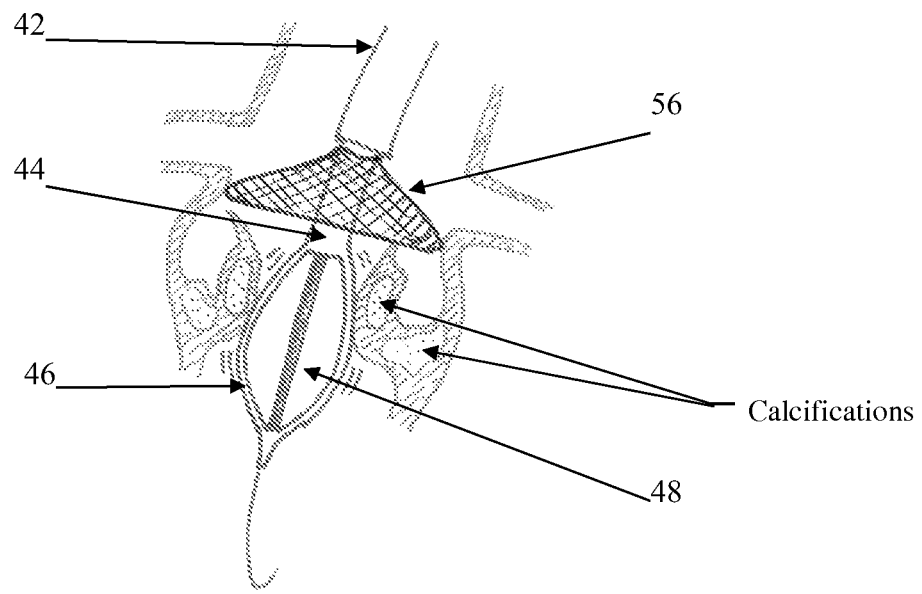
FIG. 17 is a simplified illustration of an optional addition of an embolic protection net onto the impactor catheter of FIG. 13, in accordance with a non-limiting embodiment of the invention.

Reference is now made to FIG. 17, which illustrates an optional addition of an embolic protection net (also called sleeve) 56 onto the impactor catheter. Net 56 can be made of a metal wire-mesh or a solid material covering all or part of the aortic cross section, in order to capture any emboli that might get created by fracturing the calcifications. Net 56 can be designed to fold into the catheter and out of the catheter, using external shaft 42 as a cover for net extension and retrieval.

Figure 18:
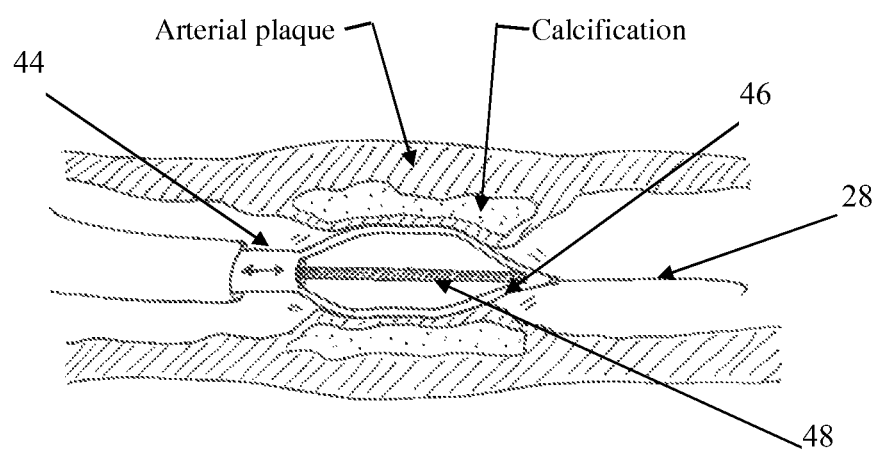
FIG. 18 is a simplified illustration of another application of the impactor catheter, namely the dilation of calcified arterial plaque, as a stand alone treatment, or as preparation for further treatment such as stenting, in accordance with a non-limiting embodiment of the invention.

Reference is now made to FIG. 18, which illustrates another application of the impactor catheter, namely the dilation of calcified arterial plaque, as a stand alone treatment, or as preparation for further treatment such as stenting. The impactor catheter is delivered into the lesion (arterial plaque) over guide-wire 28. The internal shaft 48 is pulled backwards to extend/bend the impact-producing wire arches 46, so they make sufficient contact and exert force on the plaque. The impact-delivering shaft 44 is now activated to generate impact on the calcified plaque and fracture the calcifications. Fracturing the calcifications facilitates more effective dilation of the plaque.

Figure 19:
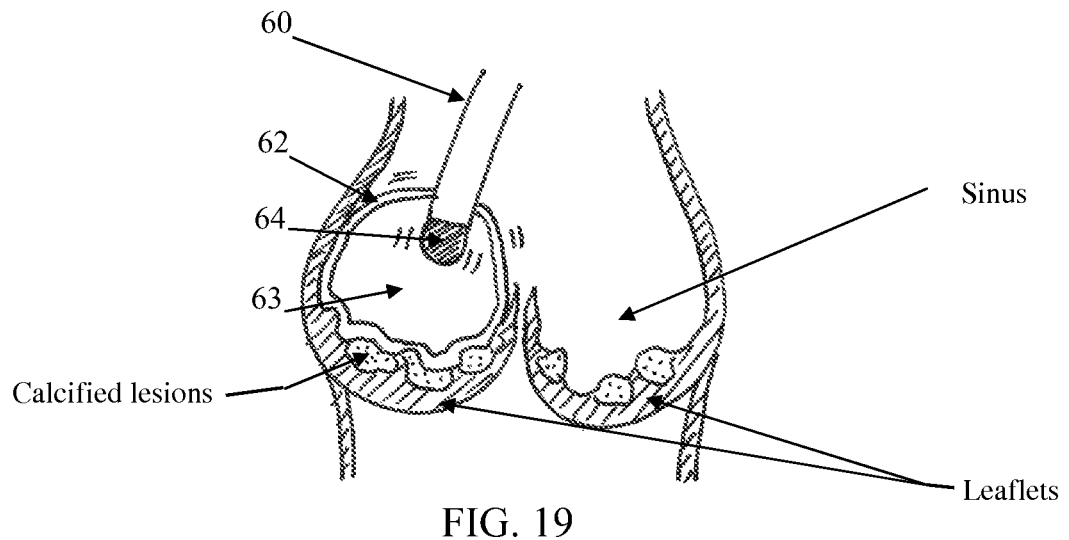
FIG. 19 is a simplified illustration of a percutaneous device for fracturing calcifications in heart valves and for increasing the flexibility of the calcified leaflets prior to dilating the valve, in accordance with yet another non-limiting embodiment of the present invention.

Reference is now made to FIG. 19, which illustrates a percutaneous device 60 for fracturing calcifications in heart valves and for increasing the flexibility of the calcified leaflets prior to dilating the valve, in accordance with yet another non-limiting embodiment of the present invention. Device 60 (also referred to as catheter 60) can be delivered (trans-apically, trans-femorally or using any other approach) to the vicinity of the calcified leaflets. In FIG. 19, catheter 60 is shown to be positioned in one of the sinuses. A balloon 62 is inflated with a fluid 63, such as but not limited to saline, or any other fluid known in the art, in order to create sufficient mechanical "coupling" or contact between the leaflet and a distal tip 64 of the catheter 60. Tip 64 is then vibrated, using techniques that will be shown below, and the vibration is transferred by balloon 62 to the leaflet. For a certain range of vibration frequencies and amplitudes, the leaflet will vibrate so that some of the calcific deposits will be fractured into smaller pieces, making the leaflet more flexible. Contact between the leaflet and the vibrating device can be from the aortic side, ventricle side, or both. This embodiment can also be used after that described in FIG. 10, as an alternative embodiment to the wire loops for delivering impact.

Figure 20:
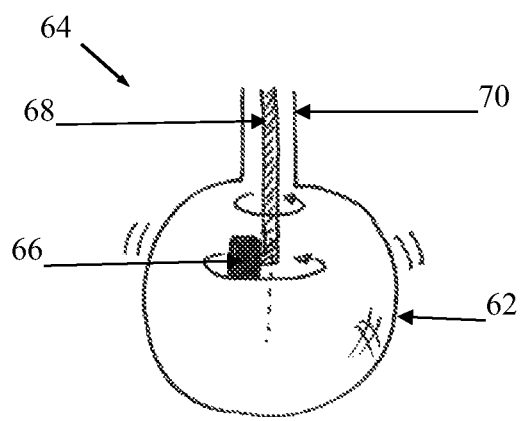
FIG. 20 is a simplified illustration of a non-limiting embodiment of the vibrating catheter tip of the device of FIG. 19.

Reference is now made to FIG. 20, which illustrates a non-limiting embodiment of the vibrating catheter tip 64. A weight 66 is connected off-axis to a rotating element 68 that rotates within an external shaft 70 of the fracturing catheter 60. The rotation can be generated by a motor connected to the proximal side of the catheter (not shown), or by a miniature motor integrated at the distal side of the catheter (not shown). Rapidly rotating the off-axis weight 66 creates vibratory motion of the catheter tip.

Figure 21:
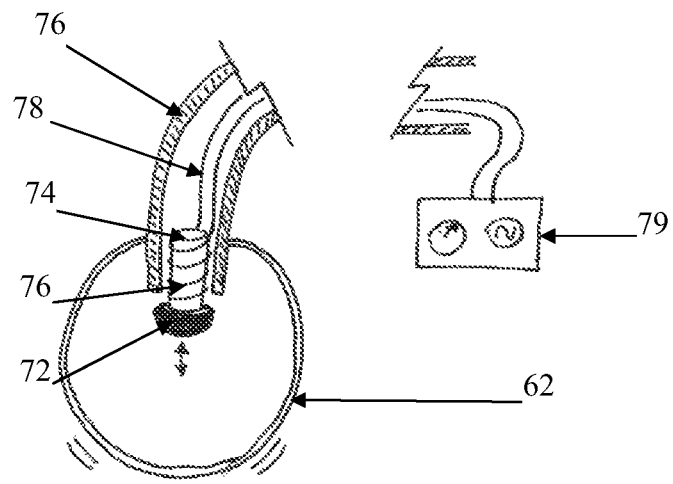
FIG. 21 is a simplified illustration of an alternative embodiment for a fracturing catheter with a vibrating tip.

Reference is now made to FIG. 21, which illustrates an alternative embodiment for a fracturing catheter with a vibrating tip. A weight 72 is mounted on a cylindrical magnet 74 that is flexible to move back and forth within a coil 76 incorporated in an external shaft. Coil leads 78 are connected at the proximal part of the catheter to an AC voltage/current generator 79. When AC current is driven through coil 76, magnet 74 and weight 72 vibrate back and forth at a selected amplitude and frequency. Balloon 62 can be inflated to make sufficient contact with the valve leaflet (not shown), in order to transfer the vibratory motion to the leaflet and fracture the calcific deposits.

Figure 22:
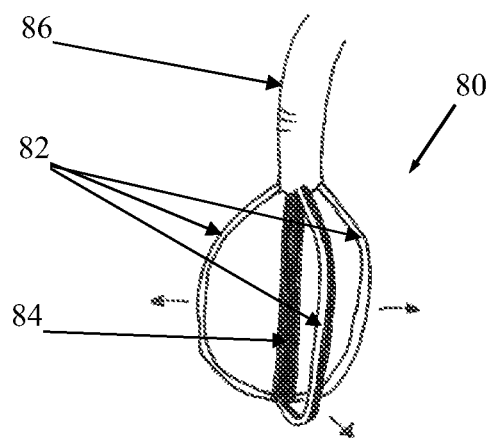
FIG. 22 is a simplified illustration of a percutaneous device (catheter) for fracturing calcifications in heart valves and for increasing the flexibility of the calcified leaflets prior to dilating the valve, in accordance with yet another non-limiting embodiment of the present invention.

Reference is now made to FIG. 22, which illustrates a percutaneous device (catheter) 80 for fracturing calcifications in heart valves and for increasing the flexibility of the calcified leaflets prior to dilating the valve, in accordance with yet another non-limiting embodiment of the present invention. One or more extendable fracturing (arcuate) arms 82, which are disposed at the distal side of the catheter, extend radially from the catheter center and are retractable (foldable) back into the catheter. For example, one side of each arm 82 may be connected to an internal element (shaft) 84 and another side connected to an external sheath (shaft) 86. By pushing or pulling the internal element 84 within the external sheath 86 or vice versa, the arms 82 can be folded or extended. Arms 82 are provided with sharp external edges and have sufficient stiffness in the radial direction so as to apply a cutting radial force against the valve tissue, so as to fracture the calcific deposits when extended.

Figure 23:
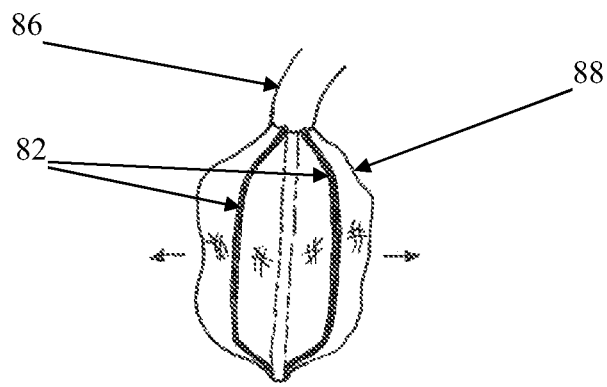
FIG. 23 is a simplified illustration of a fracturing catheter, in accordance with a non-limiting embodiment of the present invention.

Reference is now made to FIG. 23 shows another version of the fracturing catheter. In this version, the extendable arms 82 are mounted on a balloon 88. When balloon 88 is inflated, it applies a radial force that pushes arms 82 outwards to extend and cut through calcific deposits. When balloon 88 is deflated, arms 82 fold back into catheter sheath 86. Alternatively to using a balloon, the embodiment of FIG. 22 can be used with an additional coverage all around the extendable arms using plastic or graft material (that can be stretched or folded when the arms are extended or retracted). Such coverage can improve the distribution of radial forces on the leaflets and provide some protection against injury to the leaflet surface or embolization.

Figure 24:
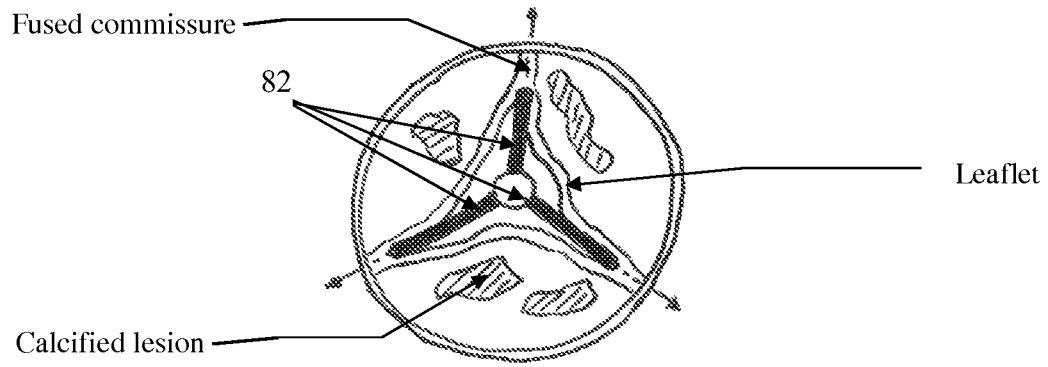
FIG. 24 is a simplified top sectional view (from the aortic side) of the fracturing catheter with three extendable arms, positioned inside the native valve.

Reference is now made to FIG. 24, which illustrates a top sectional view (from the aortic side) of the fracturing catheter with extendable arms 82, when it is positioned inside the native valve. In the example shown in FIG. 24, three extendable fracturing arms 82 are incorporated in the catheter. The catheter is partly advanced through the center of the valve, and rotated so that the extendable arms are directed against the commissures. Trans-esophageal echo (TEE) can be used to perform this positioning. Arms 82 are then extended radially so that they cut through fused leaflets in order to dilate the valve.

Figure 25:
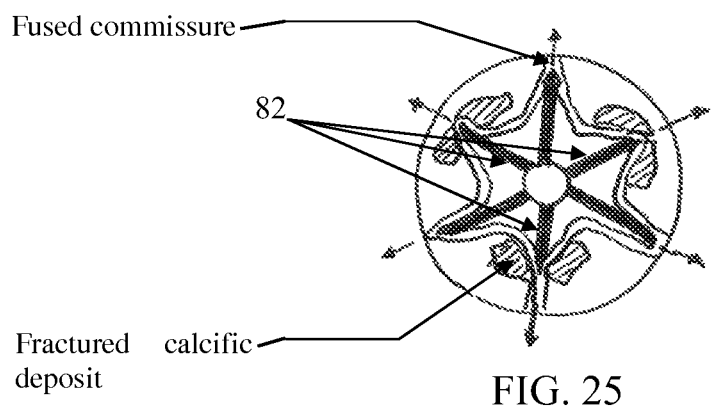
FIG. 25 is a simplified top sectional view (from the aortic side) of another embodiment of a fracturing catheter with six extendable arms, positioned in the native valve.

Reference is now made to FIG. 25, which illustrates a top sectional view (from the aortic side) of another embodiment of a fracturing catheter with extendable arms 82, when positioned in the native valve. In the example shown in FIG. 25, six extendable fracturing arms 82 are incorporated in the catheter, in order to cut through fused commissures and to fracture the center of each of the calcified leaflets. When arms 82 are extended, the large calcific deposits are fractured into smaller pieces, allowing better dilation of the native valve. It can be readily understood that the invented device can be designed to have any number of extendable arms, whether balloon mounted or without a balloon. The arms can be designed to form different functions. For example, some of the arms can be designed for simply stabilizing/positioning the catheter and not for cutting/fracturing the commissures or leaflets. In such cases their profile is not sharp. The arms designated for fracturing or cutting through tissue can be specifically designed to have sharp profiles. The arms can be designed to have adjustable angular positions, so that by using image guidance, such as trans-esophageal echo (TEE), they can be specifically positioned against commissures, leaflets, calcific deposits, etc. The arms can also be designed so that each individual arm has an adjustable radial distance of extension and adjustable force against the tissue.

Figure 26:
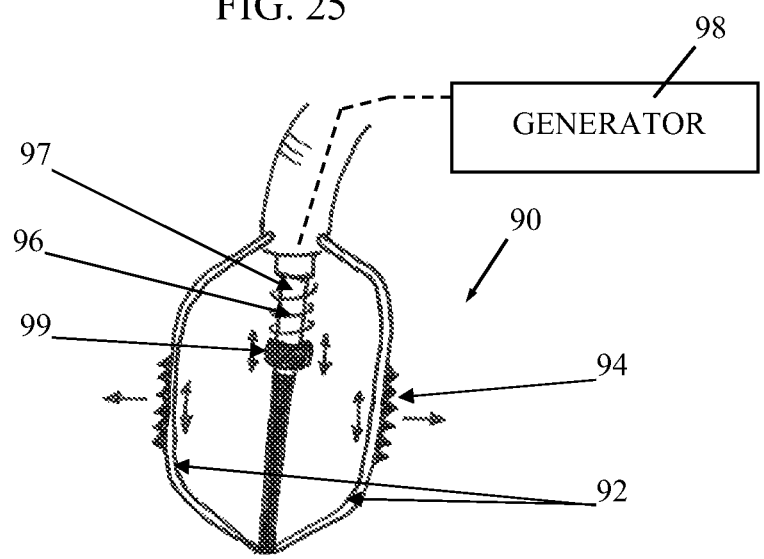
FIG. 26 is a simplified illustration of a fracturing catheter with extendable fracturing arms, in accordance with another embodiment of the invention.

Reference is now made to FIG. 26, which illustrates a fracturing catheter 90 with extendable fracturing arms 92, in accordance with another embodiment of the invention. In this embodiment, the fracturing or cutting capabilities of arms 92 are significantly improved by allowing them to saw through tissue. If the valve is heavily calcified, it may not be sufficient to simply push sharp arms against the calcific deposits in order to fracture them. In such cases, additional means may be necessary to allow the arms to cut through hard tissue. In FIG. 26, the extendable arms 92 are designed to have sharp saw teeth 94 that can be moved or vibrated up and down along the catheter axis, while the arms 92 are extended to push against the tissue. At certain ranges of vibratory amplitude and frequency, hard tissues can be sawn while soft tissue can be left unharmed, which may be an important safety requirement of the device. Vibratory or translational motion can be generated by any methods known in the art, including those described above. In the non-limiting embodiment illustrated in FIG. 26, electromagnetic means were used. An electrical coil 96, driven by an external AC generator 98, moves a sliding magnet 97 attached to a weight 99 back and forth within the catheter. Arms 92 are mechanically coupled to the vibrating electromagnet 97 so that the saw teeth 94 vibrate along the catheter axis and saw through hard tissue. Alternatively, instead of using saw teeth, the arms 92 can be covered on the external side by a rough surface that can grind or abrade the hard tissue.

Figure 27:
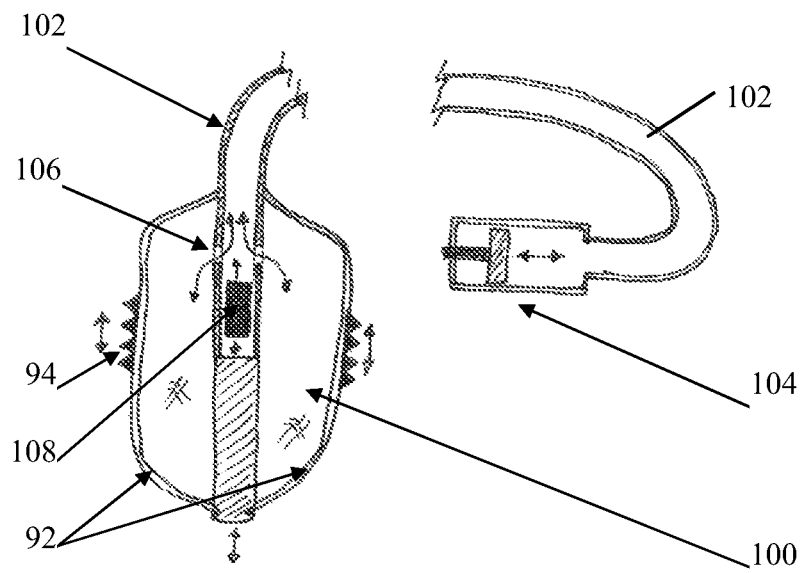
FIG. 27 is a simplified illustration of another version of the embodiment of FIG. 26.

Reference is now made to FIG. 27, which illustrates another version of the embodiment of FIG. 26. Extendable arms 92 with saw teeth 94 are mounted on a balloon 100, inflatable via an inflation tube 102 that runs throughout the length of the catheter with an inflation pump 104 on the proximal side. Pump 104 can increase the pressure in tube 102 to inflate balloon 100 through inflation holes 106 or decrease the pressure to deflate balloon 100. A weight 108 is disposed at the tip of the catheter, distally of inflation holes 106, so that it has room to move back and forth within the catheter tip, based on the fluid pressure applied by pump 104. Pump 104 can be driven by a motor to create small but rapid pressure changes around an average pressure set by the operator, so that in addition to inflating or deflating the balloon, weight 108 is influenced by these rapid pressure changes and it vibrates at a selected frequency and amplitude to cause the catheter tip and extendable arms 92 to vibrate and saw through hard tissue.

Figure 28:
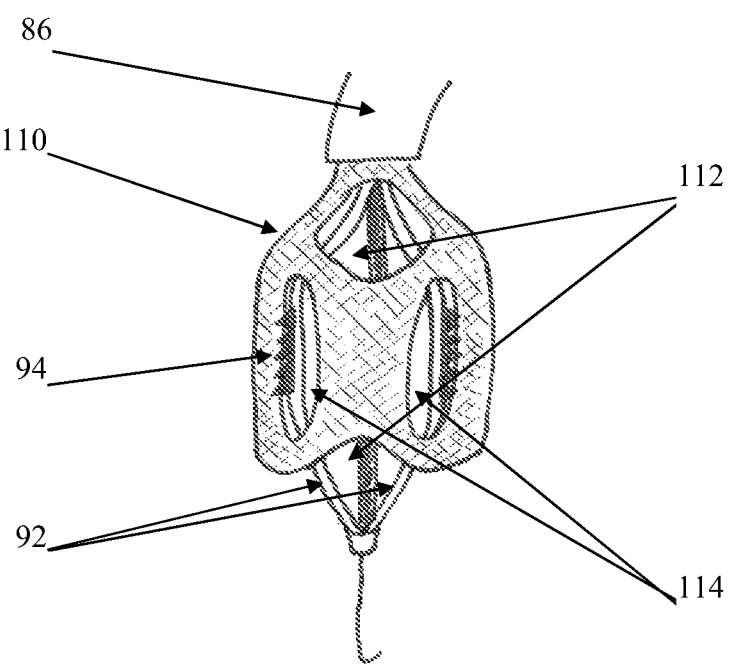
FIG. 28 is a simplified illustration of an optional add-on component to the fracturing catheter, namely a protective sleeve, in accordance with an embodiment of the invention.

Reference is now made to FIG. 28, which illustrates an optional add-on component to the fracturing catheter, namely a protective sleeve 110. Protective sleeve 110 is designed to hold the leaflets in place during the fracturing/sawing/dilation procedure in order to prevent embolization of calcific deposits and leaflet tissue into the aorta and coronary arteries. Protective sleeve 110 can be a self expanding or balloon expandable thin metal mesh that has flow openings 112 on the distal and proximal sides in order to allow blood flow through the center of the valve, unless a balloon is used for dilation. Sleeve 110 may also have several elongated saw openings 114 on its circumference in order to allow the fracturing arms 92 with saw teeth 94 to make contact with the leaflet tissue. Upon delivery of the fracturing catheter into the valve, sleeve 110 can be extended to make contact with the leaflets. Arms 92 can then be extended and operated to saw the leaflets through the openings 114 in sleeve 110. When the leaflets are fully dilated, arms 92 can be folded back into the catheter (not shown) and sleeve 110 can be kept in place until the new valve is positioned. Upon positioning the new valve, sleeve 110 can be gently pulled away and folded into the fracturing catheter.

Figure 29:
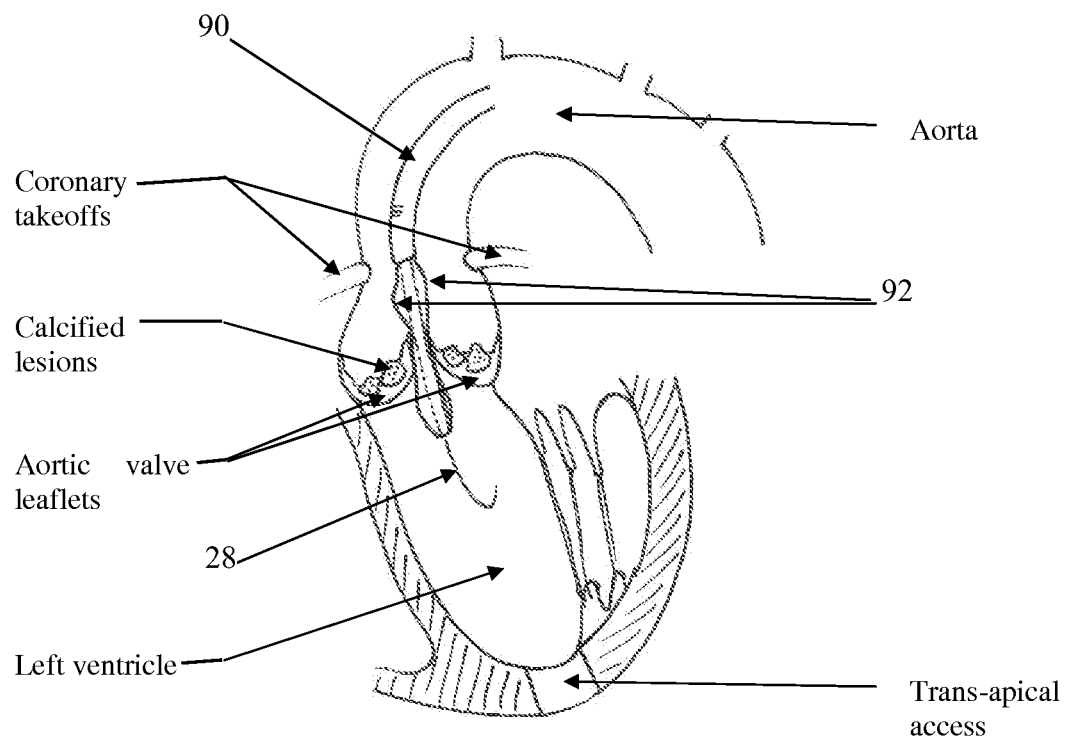
FIGS. 29-31 are simplified illustrations of a percutaneous procedure for fracturing the calcified valve leaflets prior to implanting a new valve, in accordance with an embodiment of the invention, wherein in FIG. 29, the fracturing catheter is delivered over a guide wire into the valve from the aortic side.
Figure 30:
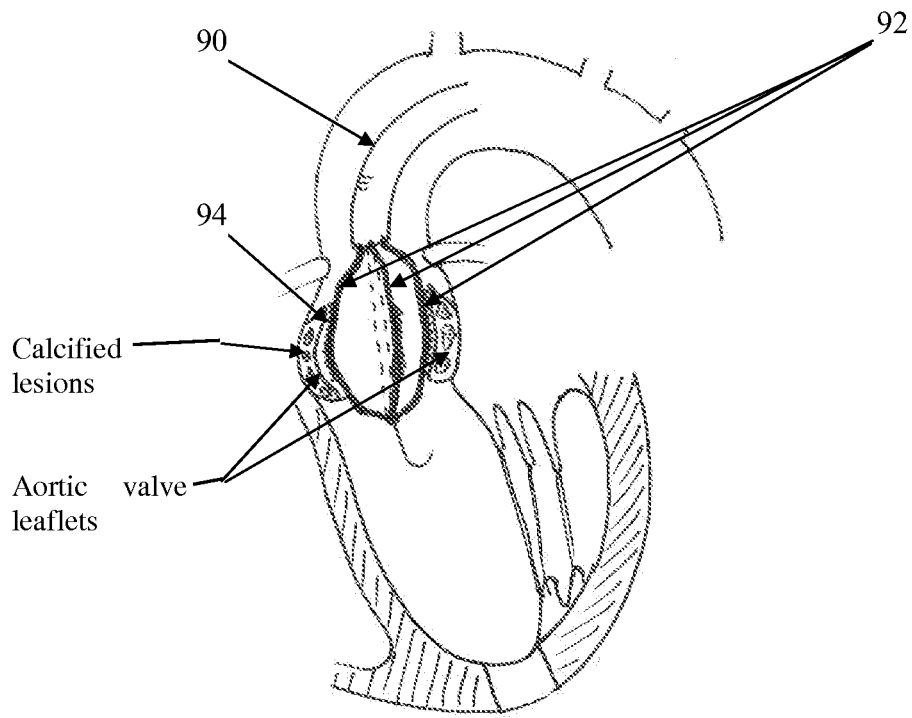
Figure 31:
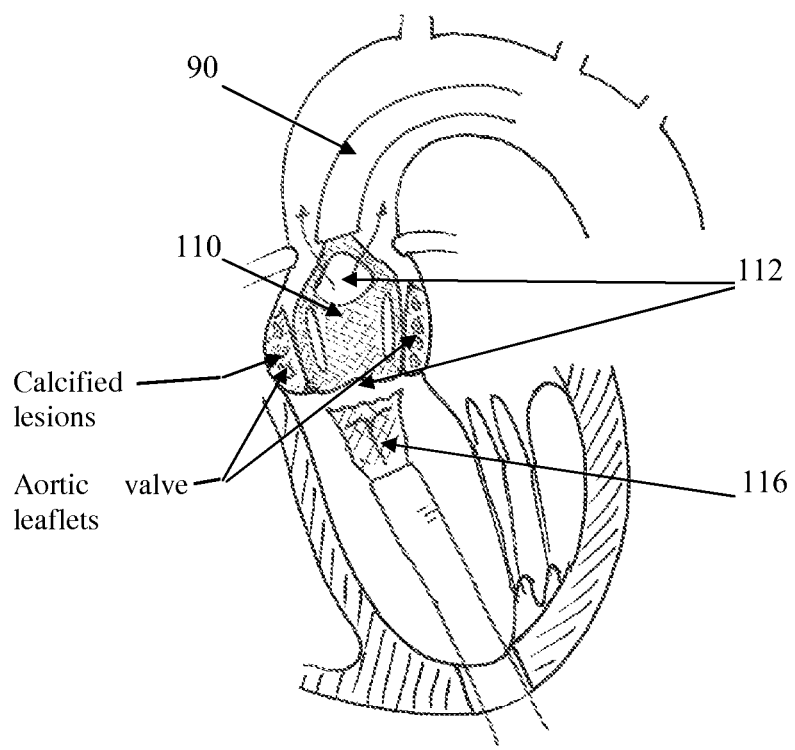

Reference is now made to FIGS. 29-31, which illustrate a percutaneous procedure for fracturing the calcified valve leaflets prior to implanting a new valve 116 (FIG. 31), in accordance with an embodiment of the invention. In this example, a trans-femoral approach has been selected. In FIG. 29, the fracturing catheter 90 is delivered over guide wire 28 into the valve from the aortic side, while delivering the new valve 116 (FIG. 31) can be done immediately afterwards using the same approach or simultaneously using the trans-apical approach. When the fracturing catheter 90 is delivered into the native valve, the extendable arms 92 are in a folded position. In embodiments with a balloon, the balloon is deflated (not shown) at this stage. The extendable arms 92 are positioned so that any saw teeth 94 or abrasion surfaces, if implemented (not shown), reside in the valve plane.

In FIG. 30, the extendable fracturing arms 92 are gradually extended (by any method such as the methods described earlier). At the same time, the vibration mechanism, if implemented (whether hydraulic, electromagnetic, etc. as described above), is activated in order to facilitate selective and effective fracturing of calcification by delivering impact or by sawing through hard tissue. Trans-esophageal echo (TEE) can be used to monitor the angular position of the arms 92 and the extent to which they fracture or cut through calcification while not injuring soft tissue (not shown). As the extendable arms 92 extend and fracture or saw through the calcified lesions, the leaflets get pushed aside and the valve is dilated to make room for the new valve.

In FIG. 31, protective sleeve 110 is deployed, and fracturing arms 92 are retracted back into the catheter 90. This leaves protective sleeve 110 in place, thereby holding the leaflets with calcified lesions so that they do not embolize. Blood flow is maintained through the flow openings 112. The new valve 116 can now be delivered into the required position through the distal flow opening 112 in sleeve 110. When the new valve 116 is almost fully expanded (not shown) the protective sleeve 110 can be gently pulled out, and the new valve 116 can be fully expanded.

In addition to fracturing and dilating the native valve, and possibly protecting against embolization until the new valve is in position, it may be advantageous, or even required in some cases, to cut and completely retrieve the native valve leaflets. Reference is now made to FIGS. 32-35, which describe an embodiment for a retrieving device and a method for using it.

Figure 32:
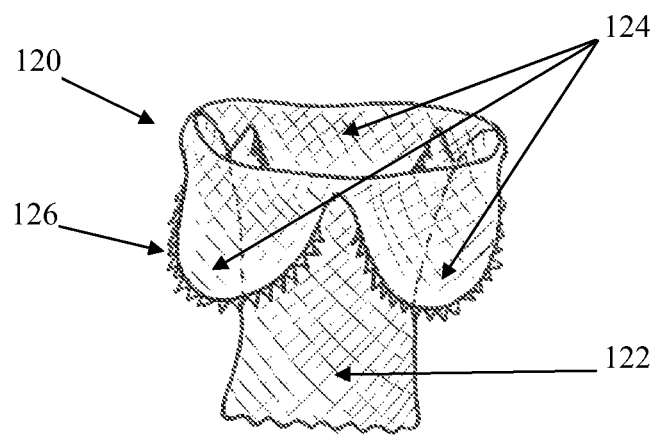
FIG. 32 is a simplified illustration of a percutaneous retrieving device for retrieving a native valve, constructed and operative in accordance with a non-limiting embodiment of the present invention.

Reference is now made to FIG. 32, which illustrates a percutaneous retrieving device 120 for retrieving a native valve, constructed and operative in accordance with a non-limiting embodiment of the present invention. Device 120 is preferably, but not necessarily, made of a thin metal mesh that can be expanded or retracted into a delivery system. Device 120 has a central lumen 122 that is intended to pass through the center of the native valve and expand to allow the implantation of the new valve within the central lumen. In addition, device 120 has semi-lunar extensions 124 (e.g., two or three) that are folded outwards and are intended to fit into the sinuses of a bicuspid or tricuspid native valve. The external edges of the extensions 124 are designed to fit the semi-lunar shape of the attachment lines between the leaflets and the aortic wall. These edges may also be designed to have saw teeth 126 or rough surfaces so that when vibrated, they can facilitate cutting or sawing of the leaflets as close as possible to the attachment lines of the leaflets with the aortic wall.

Figure 33:
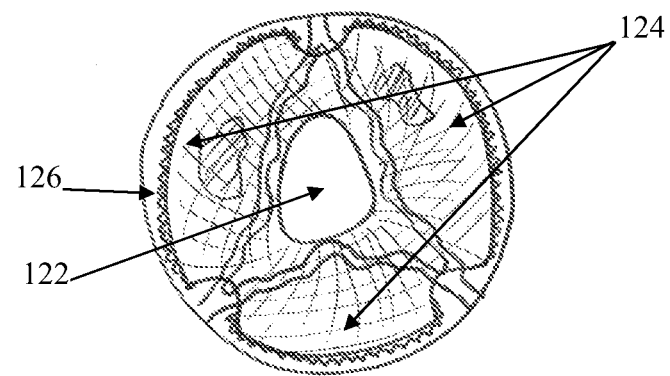
FIG. 33 is a simplified illustration of the retrieving device of FIG. 32 viewed from above (the aortic side) when it is extended and positioned in the aortic valve.

FIG. 33 shows the retrieving device of FIG. 32 as it is viewed from above (the aortic side) when it is extended and positioned in the aortic valve. The central lumen 122 extends through the center of the valve and the sinus extensions 124 are folded into the three sinuses so that their external edges with saw teeth 126 approximate the attachment lines of the leaflets and the aortic wall.

Figure 34:
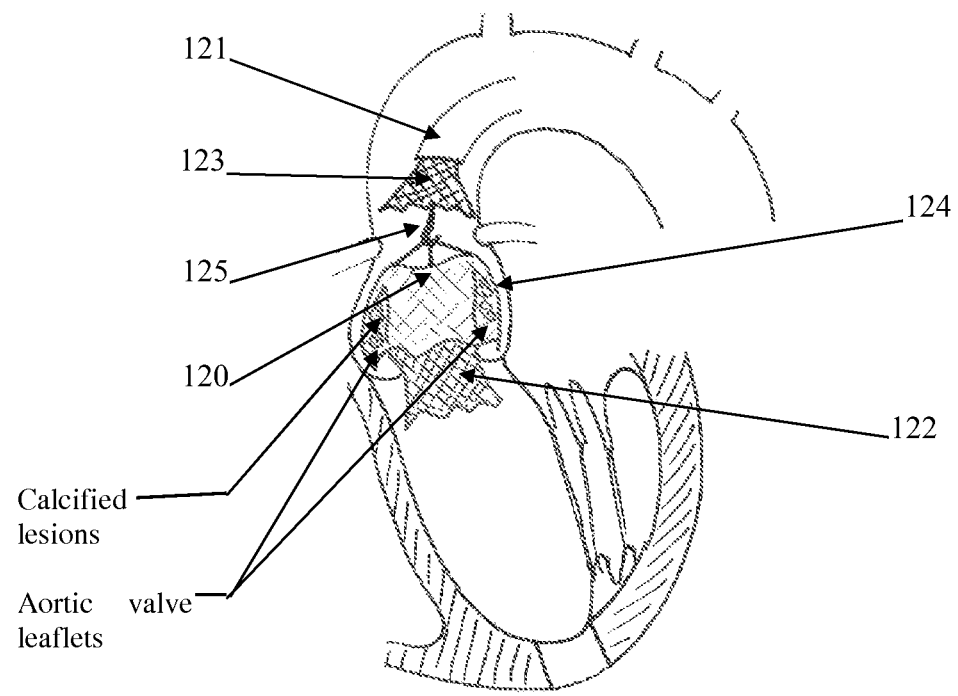
FIG. 34 is a simplified illustration of the retrieving device of FIG. 32, as it is delivered and positioned within the native aortic valve.

FIG. 34 shows the retrieving device of FIG. 32, as it is delivered and positioned within the native aortic valve. The central lumen 122 extends through the center of the valve and the sinus extensions 124 are folded into the three sinuses so that their external edges with saw teeth 126 approximate the attachment lines of the leaflets and the aortic wall. It is appreciated that the native leaflets with their calcified lesions are contained in the retrieving device so that no embolization can occur into the coronary takeoffs or the ascending aorta. Furthermore, the extended central lumen allows the delivery of a new valve, using either trans-femoral or trans-apical approach (not shown). Upon positioning of the new valve, the retrieving device 120 cuts the native leaflets as much as possible along the attachment lines to the aortic wall. This can be done by using any of the methods described above for vibrating the device while pulling or pushing it against the leaflet attachment lines so that the leaflets are completely sawn or cut out (not shown).

A retrieval catheter 121 with a retrieval sheath 123 and retrieval hook 125 can be used to retrieve retrieving device 120. The retrieving device 120 is pulled by retrieving hook 125, folded back into retrieving sheath 123 of catheter 121, while holding the native calcified leaflets, and then taken outside the patient's body. In FIG. 34 the delivery and retrieval is done trans-femorally.

Figure 35:
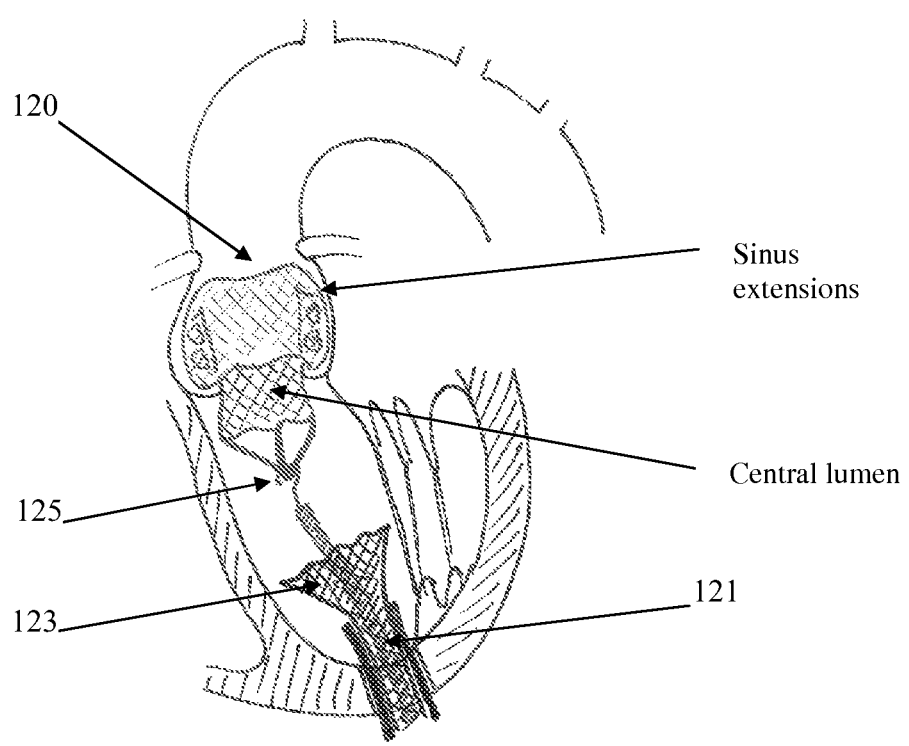
FIG. 35 is a simplified illustration of an alternative approach for retrieving the retrieving device of FIG. 32 via the apex.

Reference is now made to FIG. 35, which illustrates an alternative approach for retrieving the retrieving device 120 of FIG. 32 via the apex. Upon positioning of the retrieving device 120 and delivering the new valve (not shown), retrieval catheter 121 is delivered trans-apically, and external sheath 123 is expanded. Retrieval hook 125 is used to pull retrieving device 120 into sheath 123, and then extracted out of the body. Vibrating the retrieving device 120 in order to facilitate easier sawing of the valve leaflets can be done as described above.

Protection sleeve 110 is one embodiment for protection. Other embodiments of protection sleeves are now described that can be used to significantly improve the safety and efficacy of percutaneous implantation of aortic valves. In particular the invention describes a percutaneous protection sleeve that can be positioned in the aorta, through which large profile devices such as aortic valves, can be delivered without scraping the potentially calcified or atheromateous (covered with atheroma) aortic wall.

Figure 36:
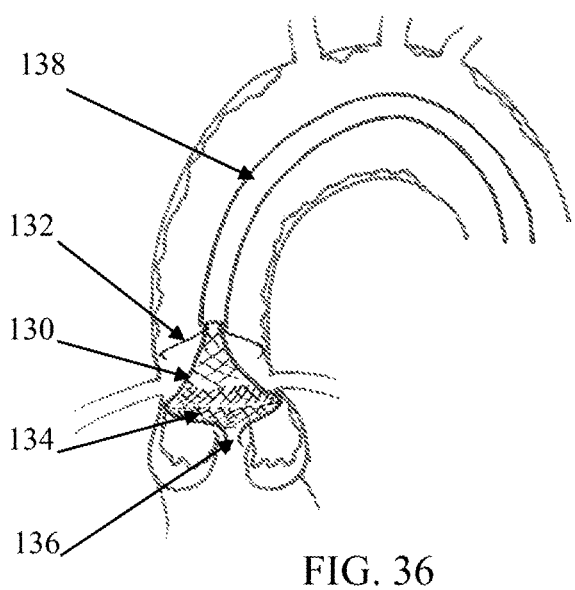
FIG. 36 is a simplified illustration of a protection sleeve, constructed and operative in accordance with a non-limiting embodiment of the present invention.

Reference is now made to FIG. 36, which illustrates a protection sleeve 130, constructed and operative in accordance with a non-limiting embodiment of the present invention. Protection sleeve 130 includes flexible anchoring arms 132 that are extendable therefrom along its length or a portion thereof. A sub-coronary net 134 extends from a distal portion of sleeve 130 along with distal wires 136. Protection sleeve 130 is initially covered by a retractable sheath 138, which also covers anchoring arms 132 (i.e., arms 132 are folded or retracted while inside retractable sheath 138.)

Protection sleeve 130 is delivered via the aorta and fixed above the aortic valve so that the distal wires 136 cross the center of the valve. Retractable sheath 138 is now retracted uncovering protection sleeve 130, which expands so that the sub-coronary net 134 makes contact with the aortic wall, just below the coronary ostia. When the sheath 138 is further retracted, the sleeve 130 is further exposed and flexible anchoring arms 132 expand to gently center and anchor the sleeve 130 to form a central conduit that does not move vis-à-vis the aortic wall.

Figure 37:
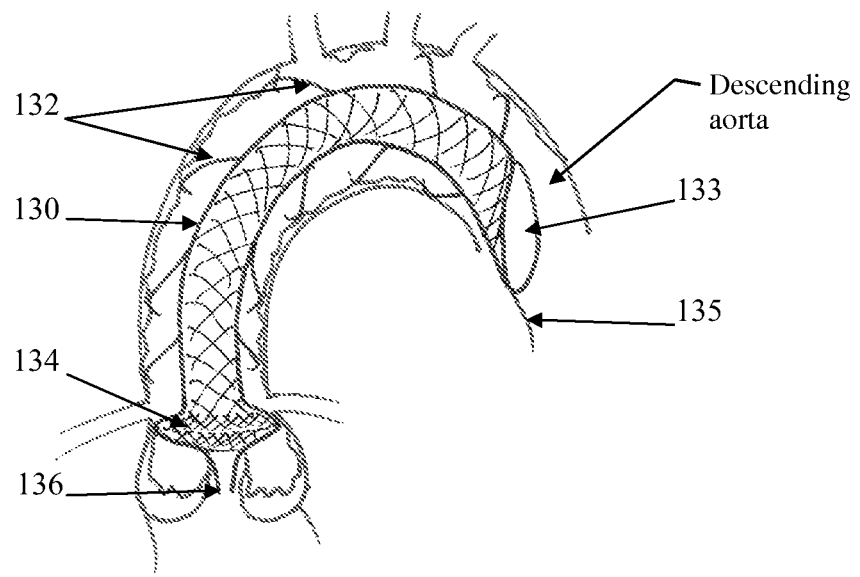
FIG. 37 is a simplified illustration of the protection sleeve in a fully expanded/deployed position.

Reference is now made to FIG. 37, which illustrates protection sleeve 130 in a fully expanded/deployed position. The distal wires 136 cross the center of the valve. The sub-coronary net 134 covers the leaflets and makes full contact with the circumference of the aorta just below the coronary ostia. The protection sleeve 130 goes all the way through the aortic arch up until the descending aorta, and is anchored to the aortic walls by anchoring arms 132 to prevent its motion. When expanded, the outer diameter of the sleeve 130 is still much lower than the diameter of the aorta, and the inner diameter of the sleeve 130 is large enough to allow even large and bulky delivery systems to easily go through its proximal opening 133 and all the way to the valve, while being kept away from the calcified or atheromateous aortic wall, so that no calcification or other tissue is scraped from the wall.

The structure and composition of the protection sleeve 130 can be any metal mesh (e.g., stainless steel, NITINOL and others), flexible plastic or graft material, or a combination thereof, that allows smooth delivery of devices through it. If made of a metal mesh, the cells can be relatively large, as they do not function to protect against embolization, but rather only to guide devices through the sleeve. The sub coronary net 134, however, is preferably designed to be dense enough in order to protect against embolization from the valve leaflets while performing manipulations on the valve. On the proximal side of the sleeve 130, one or more retrieval wires 135 extend all the way to the puncture site and outside the patient's body, in order to allow re-advancing of the retractable sheath 138 to fold back the sleeve 130 and retrieve it out of the patient's body at the end of the procedure.

Figure 38:
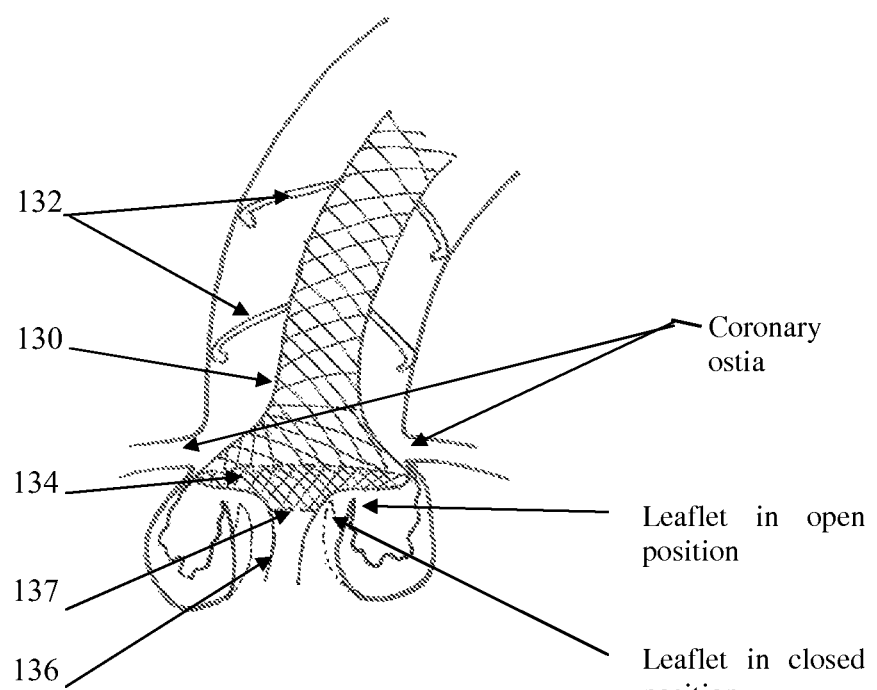
FIG. 38 is a close up view of the distal part of one embodiment of a protection sleeve.

Reference is now made to FIG. 38, which illustrates a close up view of the distal part of one embodiment of a protection sleeve. Specifically, the shape and function of the sub-coronary net 134 is noted. As long as a new valve is not deployed, the native valve needs to continue to function. Although limited in mobility due to calcification, the native valve leaflets still retain some mobility during the heart cycle between the open and closed positions, as shown. When the sleeve 130 is positioned, the sub-coronary net 134 expands, so that at its widest cross-section, it makes contact with the full circumference of the aorta, forming an enclosed region above the leaflets. Blood can continue to flow with minimal resistance through the sub-coronary net 134, through a distal ring 137 of net 134 and through the sleeve 130, while any emboli created on the upper surface of the leaflets will be captured by the net 134. The diameter of the distal ring 137 preferably matches the diameter of the valve in a closed position, so that the leaflets can fully open and close below the net 134. It may be possible to adjust the diameter of the distal ring 137 by using a wire loop or wires 136, or simply adjusting it manually prior to inserting the sleeve into the patient (not shown).

Figure 39:
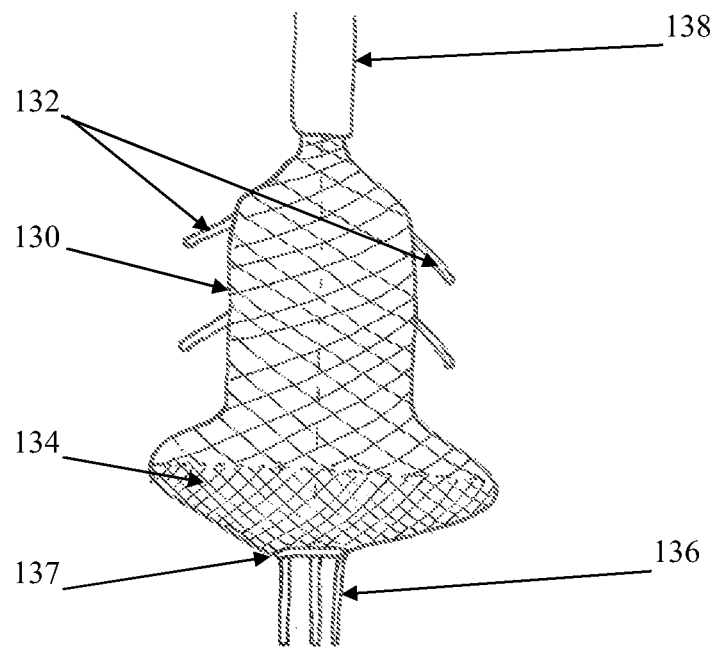
FIG. 39 is a simplified illustration of different sections of one possible embodiment of a protection sleeve.

Reference is now made to FIG. 39, which illustrates different sections of one possible embodiment of a protection sleeve 130. As mentioned above, retractable sheath 138 initially covers sleeve 130. When sheath 138 is retracted, sleeve 130 is exposed so that it expands and anchors itself with anchoring arms 132 to the aortic wall. The sub-coronary net 134 expands to a larger diameter, in order to make contact with the complete circumference of the aorta, just below the coronary ostia. The distal ring 137 (fixed or adjustable in diameter) is positioned at the level of the valve opening and the distal wires 136 cross the valve. Each component of the device can be made radiopaque in order to serve as a position marker for the new valve when implanted. As described above, the sub-coronary net 134 can be made of either a dense metal mesh or a continuous stretchable material, or both, in order to ensure that emboli will be caught by the net 134, while minimal resistance is created on aortic blood flow. The longer section of the protection sleeve 130 does not need to incorporate a dense net, but rather a simple structure that will enable smooth delivery of devices through it.

Figure 40:
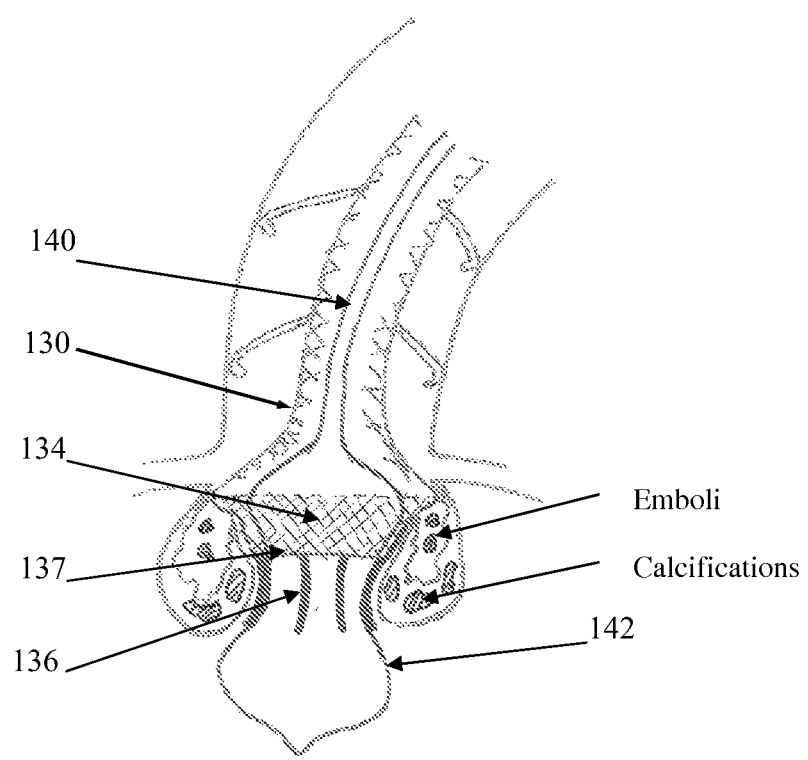
FIG. 40 is a simplified illustration of a method for dilating the valve using balloon valvuloplasty, in accordance with an embodiment of the invention.

Reference is now made to FIG. 40, which illustrates a method for dilating the valve using balloon valvuloplasty, in accordance with an embodiment of the invention. After positioning the protection sleeve 130, a balloon catheter 140 is delivered through the sleeve 130 and into the valve, using the sub-coronary net 134 and distal ring 137 as markers for positioning a valvuloplasty balloon 142. When balloon 142 is inflated, the native valve leaflets are pushed aside, while the sub-coronary net 134 maintains embolic protection in case any calcification gets dislodged. Distal ring 137 can expand to allow balloon 142 to fully inflate. When balloon 142 is deflated, distal ring 137 contracts (not shown), allowing the leaflets to function again. Distal wires 136 can be designed to perform an important function of fracturing the calcifications in the leaflets, by focusing the pressure of the inflated balloon 142 on the thin wires 136, to apply a much stronger force on the calcification, very much like the cutting balloon concept.

Figure 41:
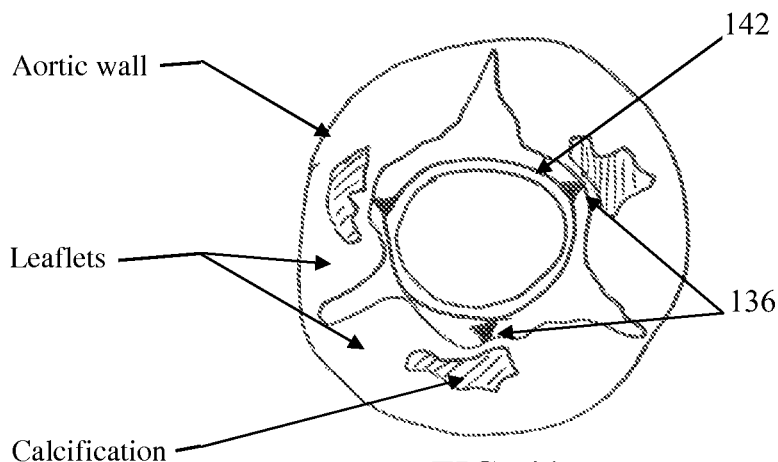
FIG. 41 is a simplified transverse cross-sectional view of a calcified tricuspid valve dilated by the balloon of FIG. 40 using distal wires to more effectively fracture the leaflet calcifications.

Reference is now made to FIG. 41, which illustrates a transverse cross-sectional view of a calcified tricuspid valve dilated by balloon 142 using distal wires 136 to more effectively fracture the leaflet calcifications, as described just before with reference to FIG. 40. The three leaflets are shown to have three large calcifications around their centers. Three distal wires 136 with sharp triangular cross-sections are shown in this specific example, although any number of wires with any profile can be used.

Figure 42:
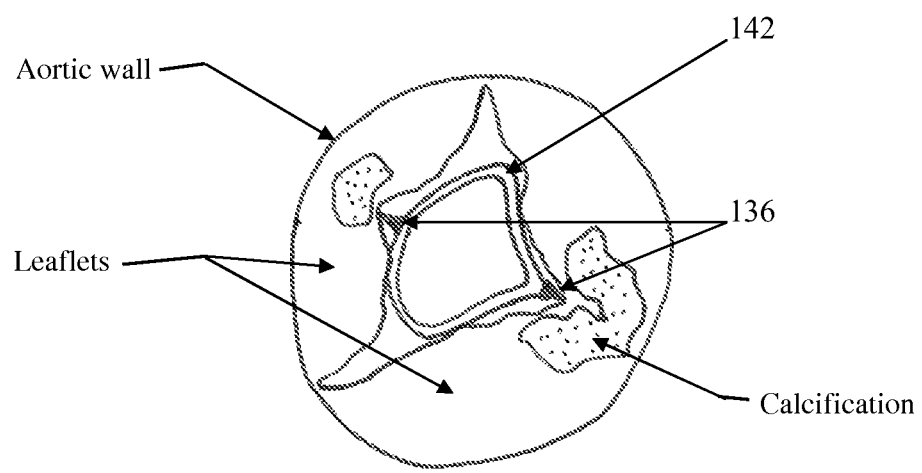
FIG. 42 is a simplified transverse cross-sectional view of a calcified bicuspid valve dilated by the balloon of FIG. 40 using distal wires to more effectively fracture the leaflet calcifications.

Reference is now made to FIG. 42, which illustrates a transverse cross-sectional view of a calcified bicuspid valve dilated by balloon 142 using distal wires 136 to more effectively fracture the leaflet calcifications, as described just before with reference to FIG. 40. The two leaflets are shown to have two large calcifications around their centers. It is common to find a large calcific deposit around the center of the larger leaflet in a bicuspid valve, called the raphe. Such a large, asymmetric calcification can be a contra-indication for percutaneous implantation of a new valve, since a stent can be under-deployed, leading to paravalvular leaks and durability issues. In FIG. 42, two distal wires 136 with sharp triangular cross-sections are shown, although any number of wires with any profile can be used. The sub-coronary net or the distal ring (not shown in FIG. 42) can be pre-shaped to align at a certain angular position within the bicuspid valve, so that the wires align with the angular position of the calcifications. In bicuspid valves, this can more effectively fracture the large calcification and enable percutaneous implantation of a new valve.

Figure 43:
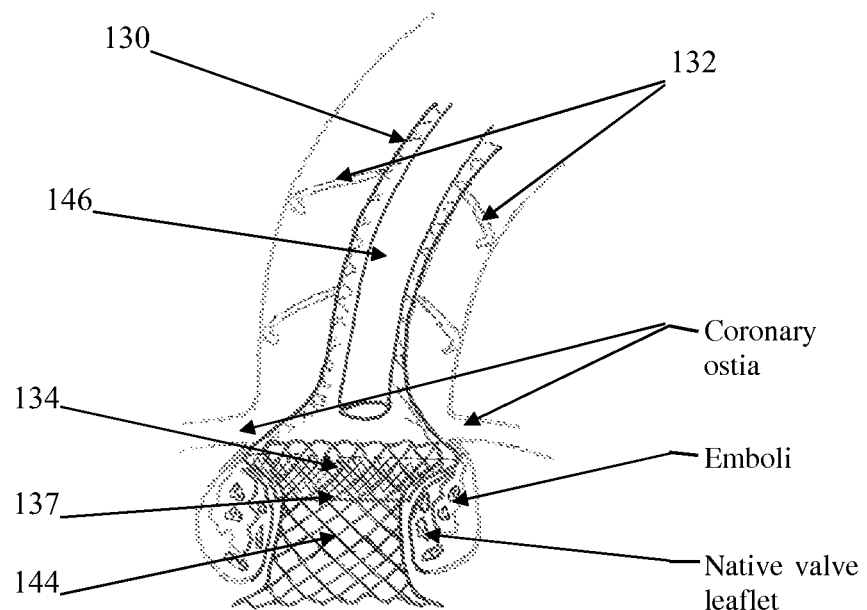
FIG. 43 is a simplified illustration of a percutaneous placement of a new valve through the protection sleeve, in accordance with an embodiment of the invention.

Reference is now made to FIG. 43, which illustrates a percutaneous placement of a new valve 144 through protection sleeve 130, in accordance with an embodiment of the invention. Protection sleeve 130 is positioned and anchored to the aortic wall by the anchoring arms 132, so that the sub-coronary net 134 makes contact with the aortic wall just below the coronary ostia, thereby covering the native valve leaflets and any emboli created during the balloon valvuloplasty procedure. A new valve delivery system 146 (of any kind known in the art) is advanced through the proximal opening (not shown) and then through the protection sleeve 130, all the way into the center of the native valve, thereby avoiding any scraping of the calcified aorta and any unwanted off-center or angled deployment of the valve. The new valve 144 can now be accurately positioned longitudinally using markers such as the distal ring 137 and sub-coronary net 134. The natural narrowing, or "shoulder", of the sub-coronary net 134 makes a good mechanical anchoring position for the new valve 144, which is now self-expanded or balloon-expanded, based on the specific valve design. The ability to use pre-positioned protection sleeve 130 for easier, safer and more accurate placement of the new valve 144 is highly advantageous.

Figure 44:
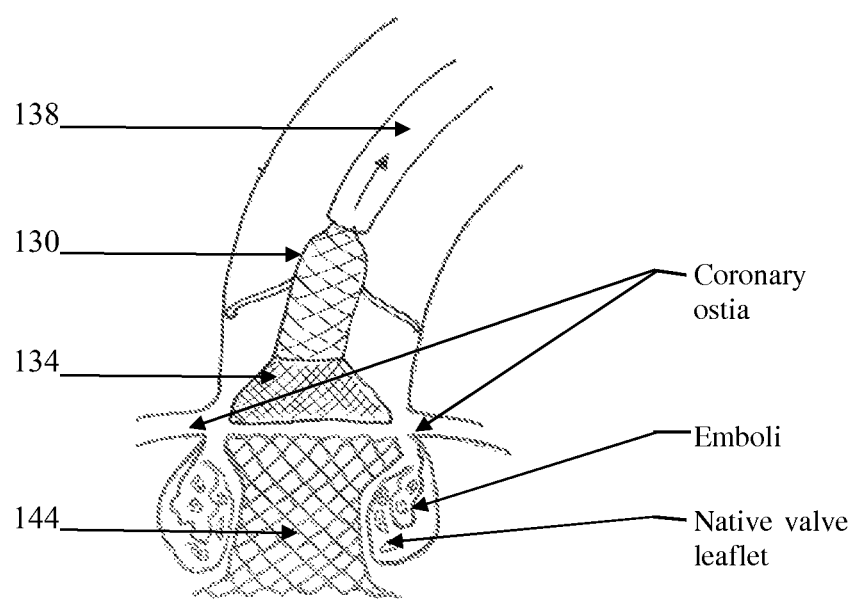
FIG. 44 is a simplified illustration of the new valve in place and the protection sleeve retracted back into a sheath for removal out of the patient's body.

Reference is now made to FIG. 44, which illustrates new valve 144 in place and protection sleeve 130 retracted back into sheath 138 for removal out of the patient's body. The sub-coronary net 134 preferably has a very smooth internal surface so that it creates minimal friction with the implanted valve 144, and does not dislodge it or cause migration when retracted. When the new valve 144 is fully expanded, the native valve leaflets are effectively folded sideways below the coronary ostia, and any emboli created during native valve manipulations are enclosed.

Figure 45:
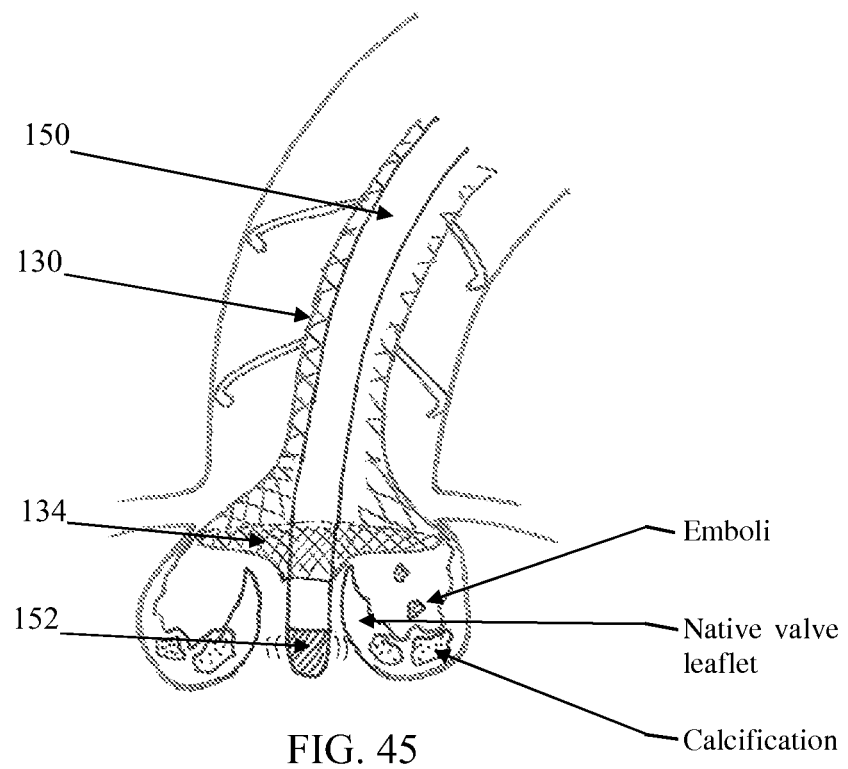
FIG. 45 is a simplified illustration of a percutaneous shockwave decalcification catheter, constructed and operative in accordance with a non-limiting embodiment of the present invention.

Reference is now made to FIG. 45, which illustrates a percutaneous shockwave decalcification catheter 150, constructed and operative in accordance with a non-limiting embodiment of the present invention. The shockwave catheter 150 can be used independently or in conjunction with the protection sleeve 130 in order to increase the pliability of the native valve leaflets and/or allow easier dilation and/or better placement of a new valve. Shockwave technology (lithotripsy) has numerous applications in medicine, such as fragmenting of kidney stones. A series of impulses of high pressure gradients are created by a shockwave source 152, such as a spark-gap, electromagnetic or piezo-electric source. Such high-pressure gradients set up shockwaves that travel through tissue and can effectively fracture hard tissue such as calcific calculi. The shockwave source can be placed either inside or outside the body, as long as sufficient acoustic impedance matching is maintained to allow the acoustic shockwaves to travel effectively to the tissue that needs to be treated.

In FIG. 45, an internal shockwave source 152 is shown delivered through the protection sleeve 130 and sub-coronary net 134 and into the plane of the native valve leaflets that are heavily calcified. Blood acts as a good impedance matching so that the shockwaves can effectively travel to hit and fracture the calcifications within the leaflets. If such fracturing creates embolization, the emboli will be captured by the sub-coronary net 134.

Figure 46:
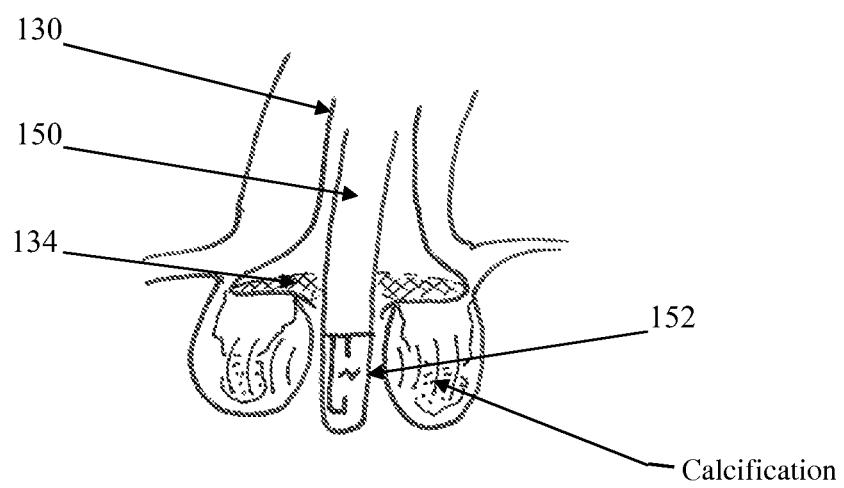
FIG. 46 is a simplified illustration of one possible embodiment of the shockwave catheter of FIG. 45.

Reference is now made to FIG. 46, which illustrates one possible embodiment of the shockwave catheter 150 described in FIG. 45. Source 152 here is a spark-gap source that creates a high-voltage spark, which generates omnidirectional shockwaves that travel and hit the calcifications in the native valve leaflets. Shockwave focusing can be applied as known in the art (e.g., parabolic or other shaped reflectors), although not shown here because the physical proximity of the spark-gap source to the leaflets may create sufficient power/pressure gradients to effectively fracture the calcifications.

Figure 47:
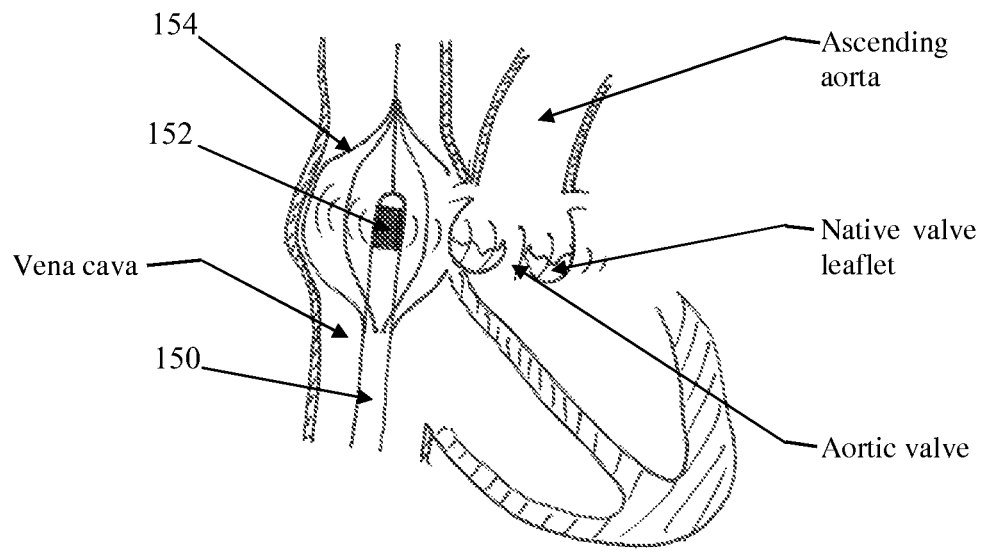
FIG. 47 is a simplified illustration of another possible configuration for the shockwave fracturing catheter.

Reference is now made to FIG. 47, which illustrates another possible configuration for shockwave fracturing catheter 150. In this version, shockwave catheter 150 has shockwave source 152 at its distal tip and further includes folded supporting structure 154. Shockwave catheter 150 is advanced through the venous system up the vena cava, until the shockwave source 152 reaches the transverse plane of the aortic valve. The supporting structure 154 is then expanded (like arms 132 described above) to fix the shockwave source 152 in place. Shockwave source 152 is then activated to transmit shockwaves that fracture the calcifications in the native valve leaflets. Protection sleeve 130 (not shown), or any other available means to capture emboli, can be used within the aorta during the procedure. Alternatively, shockwave source 152 can be placed at any other position within the patient's body, such as in the esophagus, left or right atria, left or right ventricles, etc., or completely outside the patient's body, as done in extracorporeal shockwave treatment of kidney stones. In any configuration, the acoustic wave path is sufficiently impedance-matched so that waves travel effectively to the treated valve leaflets. In addition, it may be advantageous or even necessary to increase the local shockwave power or effective pressure gradient by focusing the waves generated by one or multiple sources, into a small focal region within the treated valve leaflet.

Figure 48:
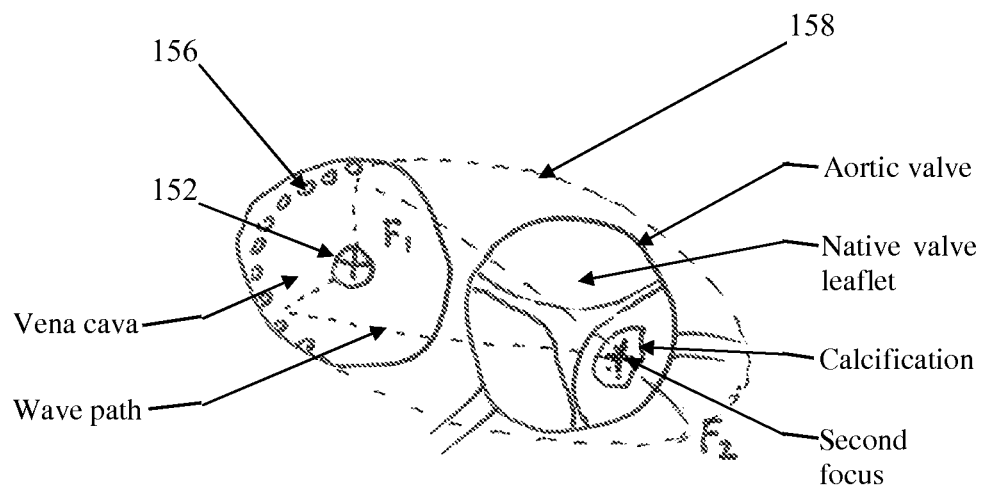
FIG. 48 is a simplified transverse cross-sectional view of one possible focusing device and method, for the vena cava catheter configuration described in FIG. 47.

Reference is now made to FIG. 48, which illustrates a transverse cross-sectional view of one possible focusing device and method, for the vena cava catheter configuration described in FIG. 47. The shockwave source 152 is placed in the vena cava at the plane of the aortic valve. A supporting structure 156 can be made of acoustic "reflectors", namely components with significantly different acoustic impedance than that of the surrounding blood. If the expanded shape of the reflectors approximates part of an imaginary ellipse 158, with shockwave source 152 positioned at one focus (F1) of the ellipse and aortic valve calcification positioned at the other focus (F2) of the ellipse, then the shockwaves produced in the direction of the reflectors will be reflected and focused onto the second focus (F2), generating a much higher local shockwave power/pressure gradient in order to fracture the calcification. Similar methods, of course, can be utilized for any shockwave configuration, whither the shockwave source is anywhere inside or outside the patient's body.

The scope of the present invention includes both combinations and subcombinations of the features described hereinabove as well as modifications and variations thereof which would occur to a person of skill in the art upon reading the foregoing description and which are not in the prior art.

What is claimed is:

1. A device for fracturing calcifications in heart valves comprising:
    an impactor catheter configured for percutaneous delivery to a heart valve;
    an impact-producing element disposed at a distal portion of said catheter and operative to vibrate and create a mechanical impact when deployed out of an external housing of said catheter and brought into contact with a calcification at a leaflet of said heart valve;
    an energy source operative to vibrate said vibrating impact-producing element so that said impact-producing element fractures the calcification without necessarily removing the calcification from the leaflet; and
    an anvil against which the calcification is struck by said impact-producing element, wherein said energy source is located at a proximal portion of said catheter.

2. The device according to claim 1, wherein said impact-producing element comprises one or more impact-producing arcuate arms that extend from a distal end thereof.

3. The device according to claim 2, wherein said impact-producing arms are retractable into said external housing of said catheter.

4. The device according to claim 2, wherein said impact-producing arms are connected to an internal shaft that is movable proximally and distally to alternatively contract and expand said impact-producing arms.

5. The device according to claim 2, wherein said impact-producing arms have adjustable angular positions.

6. The device according to claim 1, further comprising a valvuloplasty balloon mounted on a balloon shaft arranged with respect to said impact-producing element such that inflation and deflation of said balloon modifies a pressing force between said impact-producing element and hard tissue.

7. The device according to claim 1, wherein said energy source comprises an electromagnetic impact source, wherein a sliding magnet creates impact percussions.

8. The device according to claim 1, further comprising an embolic protection means disposed on said impactor catheter.

9. The device according to claim 8, wherein said protection means is shaped like a sleeve and comprises flexible anchoring arms extendable therefrom.

10. The device according to claim 9, further comprising a sub-coronary net that extends from a distal portion of said sleeve.

11. The device according to claim 10, wherein said sub-coronary net has a distal ring whose diameter matches a diameter of a native valve in a closed position.

12. The device according to claim 9, further comprising a retractable sheath into which said protection sleeve is retractable.

13. The device according to claim 9, further comprising a valvuloplasty balloon mounted on a balloon catheter arranged with respect to said impact-producing element such that inflation and deflation of said balloon modifies a pressing force between said impact-producing element and hard tissue.

14. The device according to claim 1, wherein said impact-producing element comprises a weight connected off-axis to a rotating element and a motor operative to rotate said rotating element.

15. The device according to claim 1, wherein said impact-producing element comprises a weight mounted on a cylindrical magnet arranged to move back and forth within a coil disposed in said catheter, and a voltage/current generator operative to power said coil, thereby causing said weight to vibrate back and forth at a selected amplitude and frequency.

16. The device according to claim 1, further comprising a percutaneous retrieving device for retrieving a native valve, wherein said percutaneous retrieving device comprises a mesh with a central lumen adapted for passing through a center of a native valve and to expand to allow implantation of a new valve within the central lumen, and semi-lunar extensions folded outwards from said mesh and adapted to fit into sinuses of the native valve.

17. The device according to claim 1, wherein said anvil comprises a balloon.

18. A device for fracturing calcifications in heart valves comprising:
- an impactor catheter configured for percutaneous delivery to a heart valve;
- an impact-producing element disposed at a distal portion of said catheter and operative to vibrate and create a mechanical impact when deployed out of an external housing of said catheter and brought into contact with a calcification at a leaflet of said heart valve;
- an energy source operative to vibrate said vibrating impact-producing element so that said impact-producing element fractures the calcification without necessarily removing the calcification from the leaflet; and
an anvil against which the calcification is struck by said impact-producing element, wherein said energy source is located at a distal portion of said catheter.

19. A device for fracturing calcifications in heart valves comprising:
- an impactor catheter configured for percutaneous delivery to a heart valve;
- an impact-producing element disposed at a distal portion of said catheter and operative to vibrate and create a mechanical impact when deployed out of an external housing of said catheter and brought into contact with a calcification at a leaflet of said heart valve; and
- an energy source operative to vibrate said vibrating impact-producing element so that said impact-producing element fractures the calcification without necessarily removing the calcification from the leaflet, wherein said impact-producing element comprises one or more impact-producing arcuate arms that extend from a distal end thereof, said arcuate arms being flexible enough to be deliverable in a retracted state within said external housing, and then upon reaching the valve, said arcuate arms are expandable into the valve.

\* \* \* \* \*